(12) United States Patent
Williams

(10) Patent No.: US 7,747,335 B2
(45) Date of Patent: Jun. 29, 2010

(54) IMPLANTABLE MEDICAL DEVICE HAVING PRE-IMPLANT EXOSKELETON

(75) Inventor: Michael S. Williams, Santa Rosa, CA (US)

(73) Assignee: Synecor LLC, Durham, NC (US)

( * ) Notice: Subject to any disclaimer, the term of this patent is extended or adjusted under 35 U.S.C. 154(b) by 662 days.

(21) Appl. No.: 11/009,649

(22) Filed: Dec. 10, 2004

(65) Prior Publication Data

US 2005/0154437 A1    Jul. 14, 2005

Related U.S. Application Data

(60) Provisional application No. 60/529,051, filed on Dec. 12, 2003.

(51) Int. Cl.
*A61N 1/05* (2006.01)

(52) U.S. Cl. .......................... 607/126; 607/2; 607/115; 607/116

(58) Field of Classification Search ............ 607/2, 607/4–5, 9, 32, 36–37, 40–41, 115–116, 607/120–122, 126, 128; 623/1.11, 1.13, 623/1.23, 1.38
See application file for complete search history.

(56) References Cited

U.S. PATENT DOCUMENTS

| | | | |
|---|---|---|---|
| 3,211,154 A | 10/1965 | Becker et al. | |
| 3,236,239 A | 2/1966 | Berkovits | |
| 3,258,013 A | 6/1966 | Druz | |
| 3,389,704 A | 6/1968 | Buchowski et al. | |
| 3,835,864 A * | 9/1974 | Rasor et al. | 607/36 |
| 3,865,101 A | 2/1975 | Saper et al. | |
| 3,906,960 A | 9/1975 | Lehr | |
| 3,959,706 A | 5/1976 | Mabuchi et al. | |
| 4,025,860 A | 5/1977 | Shibata et al. | |
| 4,030,509 A | 6/1977 | Heilman et al. | |
| 4,041,956 A | 8/1977 | Purdy et al. | |
| 4,096,856 A | 6/1978 | Smith et al. | |
| 4,096,866 A | 6/1978 | Fischell | |
| 4,168,711 A | 9/1979 | Cannon, III et al. | |
| RE30,366 E | 8/1980 | Rasor et al. | |
| 4,323,075 A | 4/1982 | Langer | |
| 4,326,532 A | 4/1982 | Hammar | |
| 4,332,259 A | 6/1982 | McCorkle, Jr. | |
| 4,414,986 A | 11/1983 | Dickhudt et al. | |
| 4,485,813 A | 12/1984 | Anderson et al. | |
| 4,510,551 A | 4/1985 | Brainard, II | |
| 4,530,550 A | 7/1985 | Konda | |
| 4,559,951 A | 12/1985 | Dahl et al. | |

(Continued)

FOREIGN PATENT DOCUMENTS

EP    0 030 953 B1    9/1984

(Continued)

OTHER PUBLICATIONS

File wrapper for U.S. Appl. No. 10/453,971.
File wrapper for U.S. Appl. No. 11/981,008.
File wrapper for U.S. Appl. No. 11/981,363.

(Continued)

*Primary Examiner*—Carl H Layno
*Assistant Examiner*—Jessica Sarcione

(57) ABSTRACT

Methods and apparatus for implanting a medical device within a living body. The apparatus includes an elongate sleeve positionable with a living body, such as within a blood vessel, and a medical device insertable into the sleeve. During use, the sleeve is retained within the body, and the medical device is sealed within the sleeve. The sleeve substantially avoids biological growth onto the medical device, and thus permits removal of the medical device independently of the sleeve.

12 Claims, 13 Drawing Sheets

U.S. PATENT DOCUMENTS

| | | | |
|---|---|---|---|
| 4,628,944 A | 12/1986 | MacGregor et al. | |
| 4,635,639 A | 1/1987 | Hakala et al. | |
| 4,637,397 A | 1/1987 | Jones et al. | |
| 4,662,377 A | 5/1987 | Heilman et al. | |
| 4,687,482 A | 8/1987 | Hanson | |
| 4,708,145 A | 11/1987 | Tacker, Jr. et al. | |
| 4,722,353 A | 2/1988 | Sluetz | |
| 4,727,877 A | 3/1988 | Kallok | |
| 4,736,150 A | 4/1988 | Wagner | |
| 4,825,871 A | 5/1989 | Cansell | |
| 4,827,936 A | 5/1989 | Pless et al. | |
| 4,850,357 A | 7/1989 | Bach, Jr. | |
| 4,892,102 A | 1/1990 | Astrinsky | |
| 4,900,303 A | 2/1990 | Lemelson | |
| 4,931,947 A | 6/1990 | Werth et al. | |
| 4,953,551 A | 9/1990 | Mehra et al. | |
| 4,969,463 A | 11/1990 | Dahl et al. | |
| 4,991,603 A | 2/1991 | Cohen et al. | |
| 4,996,984 A | 3/1991 | Sweeney | |
| 4,998,531 A | 3/1991 | Bocchi et al. | |
| 4,998,975 A | 3/1991 | Cohen et al. | |
| 5,010,894 A | 4/1991 | Edhag | |
| 5,014,696 A | 5/1991 | Mehra | |
| 5,044,375 A | 9/1991 | Bach, Jr. et al. | |
| 5,099,838 A | 3/1992 | Bardy | |
| 5,105,810 A | 4/1992 | Collins et al. | |
| 5,107,834 A | 4/1992 | Ideker et al. | |
| 5,129,392 A | 7/1992 | Bardy et al. | |
| 5,131,388 A | 7/1992 | Pless et al. | |
| 5,133,353 A | 7/1992 | Hauser | |
| 5,144,946 A | 9/1992 | Weinberg et al. | |
| 5,163,427 A | 11/1992 | Keimel | |
| 5,170,784 A | 12/1992 | Ramon et al. | |
| 5,170,802 A | 12/1992 | Mehra | |
| 5,174,288 A | 12/1992 | Bardy et al. | |
| 5,193,540 A | 3/1993 | Schulman et al. | |
| 5,199,429 A | 4/1993 | Kroll et al. | |
| 5,221,261 A | 6/1993 | Termin et al. | |
| 5,231,996 A | 8/1993 | Bardy et al. | |
| 5,235,977 A | 8/1993 | Hirschberg et al. | |
| 5,235,978 A | 8/1993 | Hirschberg et al. | |
| 5,235,979 A | 8/1993 | Adams | |
| 5,241,960 A | 9/1993 | Anderson et al. | |
| 5,261,400 A | 11/1993 | Bardy | |
| 5,282,785 A | 2/1994 | Shapland et al. | |
| 5,292,338 A | 3/1994 | Bardy | |
| 5,306,291 A | 4/1994 | Kroll et al. | |
| 5,314,430 A | 5/1994 | Bardy | |
| 5,324,309 A | 6/1994 | Kallok | |
| 5,334,221 A | 8/1994 | Bardy | |
| 5,342,399 A | 8/1994 | Kroll | |
| 5,356,425 A | 10/1994 | Bardy et al. | |
| 5,358,514 A | 10/1994 | Schulman et al. | |
| 5,368,588 A | 11/1994 | Bettinger | |
| 5,372,585 A | 12/1994 | Tiefenbrun et al. | |
| 5,383,907 A | 1/1995 | Kroll | |
| 5,407,444 A | 4/1995 | Kroll | |
| 5,411,546 A | 5/1995 | Bowald et al. | |
| 5,423,865 A | 6/1995 | Bowald et al. | |
| 5,423,885 A | 6/1995 | Williams | |
| 5,431,686 A | 7/1995 | Kroll et al. | |
| 5,468,254 A | 11/1995 | Hahn et al. | |
| 5,483,165 A | 1/1996 | Cameron et al. | |
| 5,487,760 A | 1/1996 | Villafana | |
| 5,509,411 A | 4/1996 | Littmann et al. | |
| 5,531,779 A | 7/1996 | Dahl et al. | |
| 5,534,015 A | 7/1996 | Kroll et al. | |
| 5,545,205 A | 8/1996 | Schulte et al. | |
| 5,551,954 A * | 9/1996 | Buscemi et al. | 623/1.15 |
| 5,591,211 A | 1/1997 | Meltzer | |
| 5,591,213 A | 1/1997 | Morgan | |
| 5,593,427 A | 1/1997 | Gliner et al. | |
| 5,593,434 A | 1/1997 | Williams | |
| 5,601,612 A | 2/1997 | Gliner et al. | |
| 5,607,454 A | 3/1997 | Cameron et al. | |
| 5,613,935 A | 3/1997 | Jarvik | |
| 5,617,853 A | 4/1997 | Morgan | |
| 5,620,470 A | 4/1997 | Gliner et al. | |
| 5,645,586 A | 7/1997 | Meltzer | |
| 5,699,796 A | 12/1997 | Littmann et al. | |
| 5,704,910 A | 1/1998 | Humes | |
| 5,716,391 A | 2/1998 | Grandjean | |
| 5,735,879 A | 4/1998 | Gliner et al. | |
| 5,735,887 A | 4/1998 | Barreras, Sr. et al. | |
| 5,735,897 A | 4/1998 | Buirge | |
| 5,749,904 A | 5/1998 | Gliner et al. | |
| 5,749,905 A | 5/1998 | Gliner et al. | |
| 5,769,077 A | 6/1998 | Lindegren | |
| 5,776,166 A | 7/1998 | Gliner et al. | |
| 5,800,460 A | 9/1998 | Powers et al. | |
| 5,803,927 A | 9/1998 | Cameron et al. | |
| 5,807,399 A | 9/1998 | Laske et al. | |
| 5,814,089 A | 9/1998 | Stokes et al. | |
| 5,827,326 A | 10/1998 | Kroll et al. | |
| 5,833,603 A | 11/1998 | Kovacs et al. | |
| 5,836,978 A | 11/1998 | Gliner et al. | |
| 5,843,132 A | 12/1998 | Ilvento | 607/10 |
| 5,849,033 A | 12/1998 | Mehmanesh et al. | |
| 5,868,792 A | 2/1999 | Ochs et al. | |
| 5,879,374 A | 3/1999 | Powers et al. | |
| 5,891,046 A | 4/1999 | Cyrus et al. | |
| 5,891,049 A | 4/1999 | Cyrus et al. | |
| 5,904,707 A | 5/1999 | Ochs et al. | |
| 5,908,447 A | 6/1999 | Schroeppel et al. | |
| 5,911,704 A | 6/1999 | Humes | |
| 5,919,210 A | 7/1999 | Lurie et al. | |
| 5,951,485 A | 9/1999 | Cyrus et al. | |
| 5,954,761 A | 9/1999 | Machek et al. | |
| 5,957,842 A | 9/1999 | Littmann et al. | |
| 5,957,956 A | 9/1999 | Kroll et al. | |
| 6,016,059 A | 1/2000 | Morgan | |
| 6,045,568 A * | 4/2000 | Igaki et al. | 623/1.11 |
| 6,047,212 A | 4/2000 | Gliner et al. | |
| 6,053,873 A | 4/2000 | Govari et al. | |
| 6,088,610 A | 7/2000 | Littmann et al. | |
| 6,119,039 A | 9/2000 | Leyde | |
| 6,141,576 A | 10/2000 | Littmann et al. | |
| 6,141,588 A | 10/2000 | Cox et al. | |
| 6,161,029 A | 12/2000 | Spreigl et al. | |
| 6,214,032 B1 * | 4/2001 | Loeb et al. | 607/1 |
| 6,219,581 B1 | 4/2001 | Schaldach et al. | |
| 6,230,061 B1 | 5/2001 | Hartung | |
| 6,231,516 B1 | 5/2001 | Keilman et al. | |
| 6,256,534 B1 | 7/2001 | Dahl | |
| 6,256,541 B1 | 7/2001 | Heil et al. | |
| 6,304,786 B1 | 10/2001 | Heil, Jr. et al. | |
| 6,330,481 B1 | 12/2001 | Van Wijk et al. | |
| 6,383,171 B1 * | 5/2002 | Gifford et al. | 604/508 |
| 6,419,692 B1 | 7/2002 | Yang et al. | |
| 6,436,068 B1 | 8/2002 | Bardy | |
| 6,442,413 B1 | 8/2002 | Silver | |
| 6,445,953 B1 | 9/2002 | Bulkes et al. | |
| 6,509,104 B2 | 1/2003 | Huang et al. | |
| 6,516,231 B1 | 2/2003 | Flammang | |
| 6,522,926 B1 | 2/2003 | Kieval et al. | |
| 6,561,975 B1 | 5/2003 | Pool et al. | |
| 6,564,807 B1 | 5/2003 | Schulman et al. | |
| 6,572,605 B1 | 6/2003 | Humes | |
| 6,584,362 B1 | 6/2003 | Scheiner et al. | |
| 6,671,547 B2 | 12/2003 | Lyster et al. | |
| 6,716,208 B2 | 4/2004 | Humes | |
| 6,723,121 B1 | 4/2004 | Zhong | |
| 6,726,714 B2 | 4/2004 | DiCaprio et al. | |
| 6,733,485 B1 | 5/2004 | Whitehurst et al. | |

| | | |
|---|---|---|
| 6,735,474 B1 | 5/2004 | Loeb et al. |
| 6,735,475 B1 | 5/2004 | Whitehurst et al. |
| 6,754,528 B2 | 6/2004 | Bardy et al. |
| 6,760,622 B2 | 7/2004 | Helland et al. |
| 6,776,784 B2 | 8/2004 | Ginn |
| 6,778,860 B2 | 8/2004 | Ostroff et al. |
| 6,783,499 B2 | 8/2004 | Schwartz |
| 6,783,543 B2 | 8/2004 | Jang |
| 6,788,974 B2 | 9/2004 | Bardy et al. |
| 6,829,504 B1 | 12/2004 | Chen et al. |
| 6,834,204 B2 | 12/2004 | Ostroff et al. |
| 6,845,267 B2 | 1/2005 | Harrison et al. |
| 6,866,044 B2 | 3/2005 | Bardy et al. |
| 6,885,895 B1 | 4/2005 | Whitehurst et al. |
| 6,907,285 B2 | 6/2005 | Denker et al. |
| 6,932,930 B2 | 8/2005 | DeSimone et al. |
| 6,933,822 B2 | 8/2005 | Haugs et al. |
| 6,941,169 B2 | 9/2005 | Pappu |
| 7,003,350 B2 * | 2/2006 | Denker et al. ............. 607/33 |
| 7,006,858 B2 | 2/2006 | Silver et al. |
| 7,054,692 B1 | 5/2006 | Whitehurst et al. |
| 7,072,171 B1 | 7/2006 | Muffoletto et al. |
| 7,082,336 B2 * | 7/2006 | Ransbury et al. ............. 607/126 |
| 7,097,665 B2 | 8/2006 | Stack et al. |
| 7,114,502 B2 | 10/2006 | Schulman et al. |
| 7,236,821 B2 | 6/2007 | Cates et al. |
| 7,239,921 B2 * | 7/2007 | Canfield et al. ............. 607/48 |
| 2001/0021840 A1 | 9/2001 | Suresh |
| 2001/0041870 A1 | 11/2001 | Gillis et al. |
| 2001/0041930 A1 * | 11/2001 | Globerman et al. ......... 623/1.16 |
| 2002/0026228 A1 | 2/2002 | Schauerte |
| 2002/0042630 A1 | 4/2002 | Bardy et al. |
| 2002/0042634 A1 | 4/2002 | Bardy et al. |
| 2002/0052636 A1 | 5/2002 | Bardy et al. |
| 2002/0072773 A1 | 6/2002 | Bardy et al. |
| 2002/0090389 A1 | 7/2002 | Humes et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0111585 A1 | 8/2002 | Lafontaine |
| 2002/0120299 A1 | 8/2002 | Ostroff et al. |
| 2002/0128546 A1 | 9/2002 | Silver |
| 2002/0133224 A1 | 9/2002 | Bajgar et al. |
| 2002/0143379 A1 | 10/2002 | Morgan et al. |
| 2002/0147486 A1 | 10/2002 | Soukup et al. |
| 2002/0183791 A1 * | 12/2002 | Denker et al. ............. 607/5 |
| 2002/0188252 A1 | 12/2002 | Bardy |
| 2003/0023177 A1 | 1/2003 | Bardy |
| 2003/0032892 A1 * | 2/2003 | Erlach et al. ............. 600/547 |
| 2003/0032998 A1 | 2/2003 | Altman |
| 2003/0036778 A1 | 2/2003 | Ostroff et al. |
| 2003/0045904 A1 | 3/2003 | Bardy et al. |
| 2003/0060863 A1 | 3/2003 | Dobak, III |
| 2003/0088278 A1 | 5/2003 | Bardy et al. |
| 2003/0097051 A1 | 5/2003 | Kolberg et al. |
| 2003/0114905 A1 | 6/2003 | Kuzma |
| 2003/0158584 A1 | 8/2003 | Cates et al. ............. 607/2 |
| 2004/0073190 A1 | 4/2004 | Deem et al. |
| 2004/0116992 A1 | 6/2004 | Wardle et al. |
| 2004/0147993 A1 | 7/2004 | Westlund et al. |
| 2004/0172090 A1 | 9/2004 | Janzig et al. |
| 2004/0207503 A1 | 10/2004 | Flanders et al. |
| 2004/0249417 A1 | 12/2004 | Ransbury et al. ............. 607/4 |
| 2004/0249431 A1 | 12/2004 | Ransbury et al. |
| 2005/0004639 A1 | 1/2005 | Erickson |
| 2005/0019370 A1 | 1/2005 | Humes |
| 2005/0043765 A1 | 2/2005 | Williams et al. ............. 607/9 |
| 2005/0043789 A1 | 2/2005 | Widenhouse et al. |
| 2005/0080472 A1 | 4/2005 | Atkinson et al. |
| 2005/0119718 A1 | 6/2005 | Coe et al. |
| 2005/0147647 A1 | 7/2005 | Glauser et al. |
| 2005/0234431 A1 | 10/2005 | Williams et al. |
| 2006/0095078 A1 | 5/2006 | Tronnes |
| 2006/0129050 A1 | 6/2006 | Martinson et al. |
| 2006/0224225 A1 | 10/2006 | Ransbury et al. |
| 2006/0241732 A1 | 10/2006 | Denker et al. |
| 2008/0058886 A1 | 3/2008 | Williams |
| 2008/0065051 A1 | 3/2008 | Williams |
| 2008/0077219 A1 | 3/2008 | Williams et al. |

FOREIGN PATENT DOCUMENTS

| | | |
|---|---|---|
| EP | 0 057 448 B1 | 7/1985 |
| EP | 0 373 953 A2 | 6/1990 |
| EP | 0 373 953 A3 | 6/1990 |
| EP | 0 424 379 B1 | 5/1991 |
| EP | 0 426 089 A2 | 5/1991 |
| EP | 0 426 089 A3 | 5/1991 |
| EP | 0 453 761 A1 | 10/1991 |
| EP | 0 526 671 A1 | 2/1993 |
| EP | 0 281 219 B1 | 7/1993 |
| EP | 0 559 932 A1 | 9/1993 |
| EP | 0 559 933 A1 | 9/1993 |
| EP | 0 570 712 A1 | 11/1993 |
| EP | 0 601 338 A1 | 6/1994 |
| EP | 0 601 340 A1 | 6/1994 |
| EP | 0 646 391 A1 | 4/1995 |
| EP | 0 669 839 B2 | 6/1995 |
| EP | 0 578 748 B1 | 5/1996 |
| EP | 0 526 671 B1 | 7/1996 |
| EP | 0 779 080 A1 | 6/1997 |
| EP | 0 799 628 A2 | 10/1997 |
| EP | 0 813 886 A2 | 12/1997 |
| EP | 0 453 761 B1 | 7/1998 |
| EP | 0 570 712 B1 | 7/1998 |
| EP | 0 601 338 B1 | 10/1998 |
| EP | 0 882 452 A1 | 12/1998 |
| EP | 0 799 628 A3 | 3/1999 |
| EP | 0 601 339 B1 | 5/1999 |
| EP | 0 813 886 A3 | 11/1999 |
| EP | 0 601 340 B1 | 7/2000 |
| EP | 1 106 202 A2 | 6/2001 |
| EP | 0 646 391 B1 | 1/2002 |
| EP | 0 892 653 B1 | 7/2003 |
| EP | 1 106 202 A3 | 3/2004 |
| EP | 0 813 886 B1 | 9/2004 |
| EP | 0 601 338 B2 | 9/2005 |
| GB | 2 157 178 A | 10/1985 |
| WO | WO 92/11898 | 7/1992 |
| WO | WO 92/17240 A1 | 10/1992 |
| WO | WO 92/20401 A1 | 11/1992 |
| WO | WO 94/07564 | 4/1994 |
| WO | WO 96/39098 | 12/1996 |
| WO | WO 97/31678 A1 | 9/1997 |
| WO | WO 98/52641 A1 | 11/1998 |
| WO | WO 99/34731 | 7/1999 |
| WO | WO 00/74557 A1 | 12/2000 |
| WO | WO 02/15824 A2 | 2/2002 |
| WO | WO 02/22208 A2 | 3/2002 |
| WO | WO 02/22208 A3 | 3/2002 |
| WO | WO 02/055136 A2 | 7/2002 |
| WO | WO 02/056796 A1 | 7/2002 |
| WO | WO 02/064206 A2 | 8/2002 |
| WO | WO 2004/004603 A1 | 1/2004 |
| WO | WO 2004/028348 A2 | 4/2004 |
| WO | WO 2004/049919 A2 | 6/2004 |
| WO | WO 2004/058100 A2 | 7/2004 |
| WO | WO 2005/000398 A2 | 1/2005 |

* cited by examiner

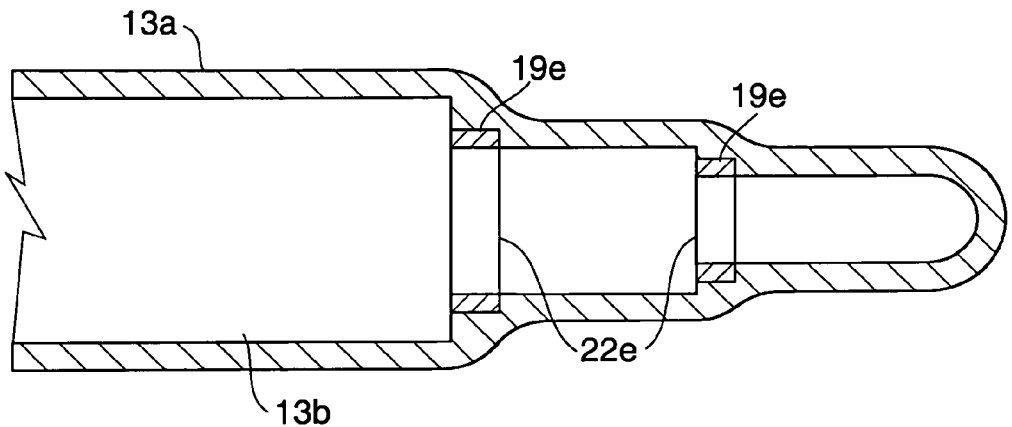
FIG. 3C
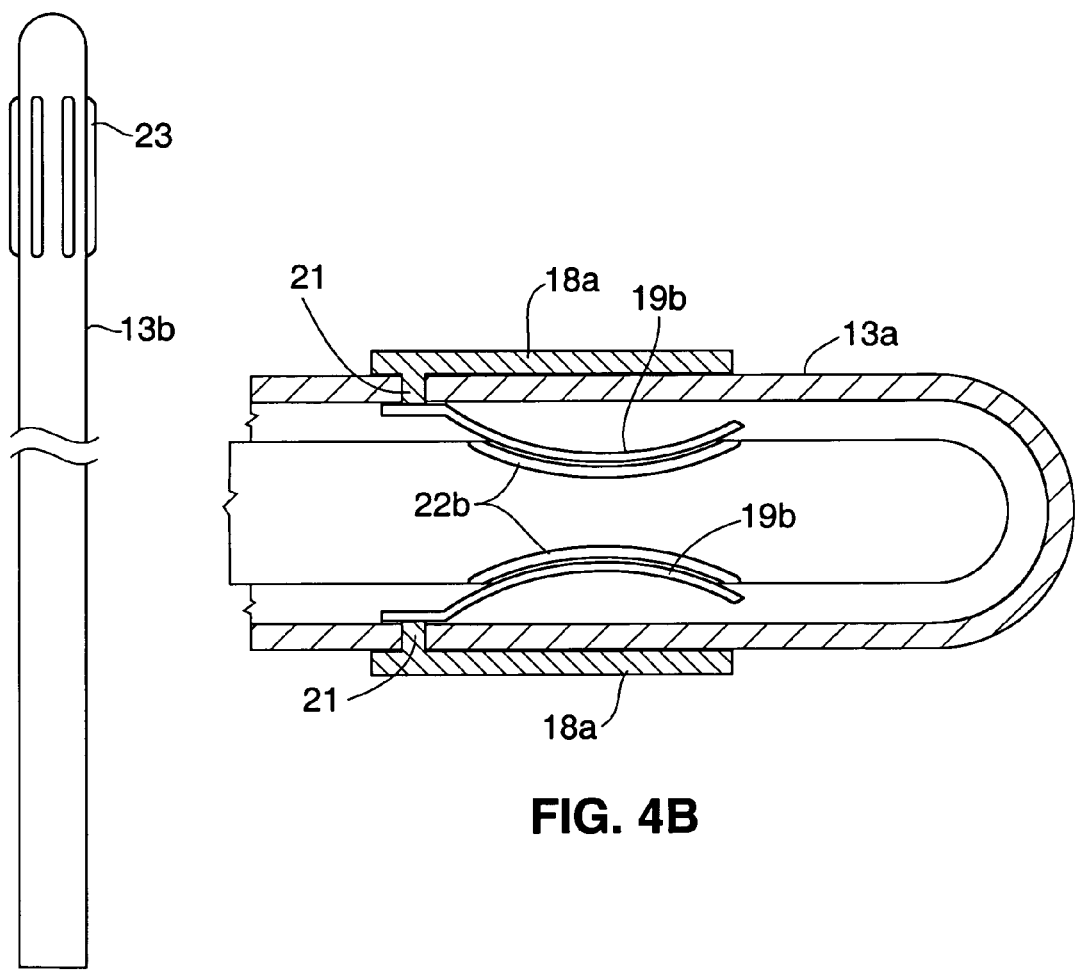
FIG. 4A
FIG. 4B

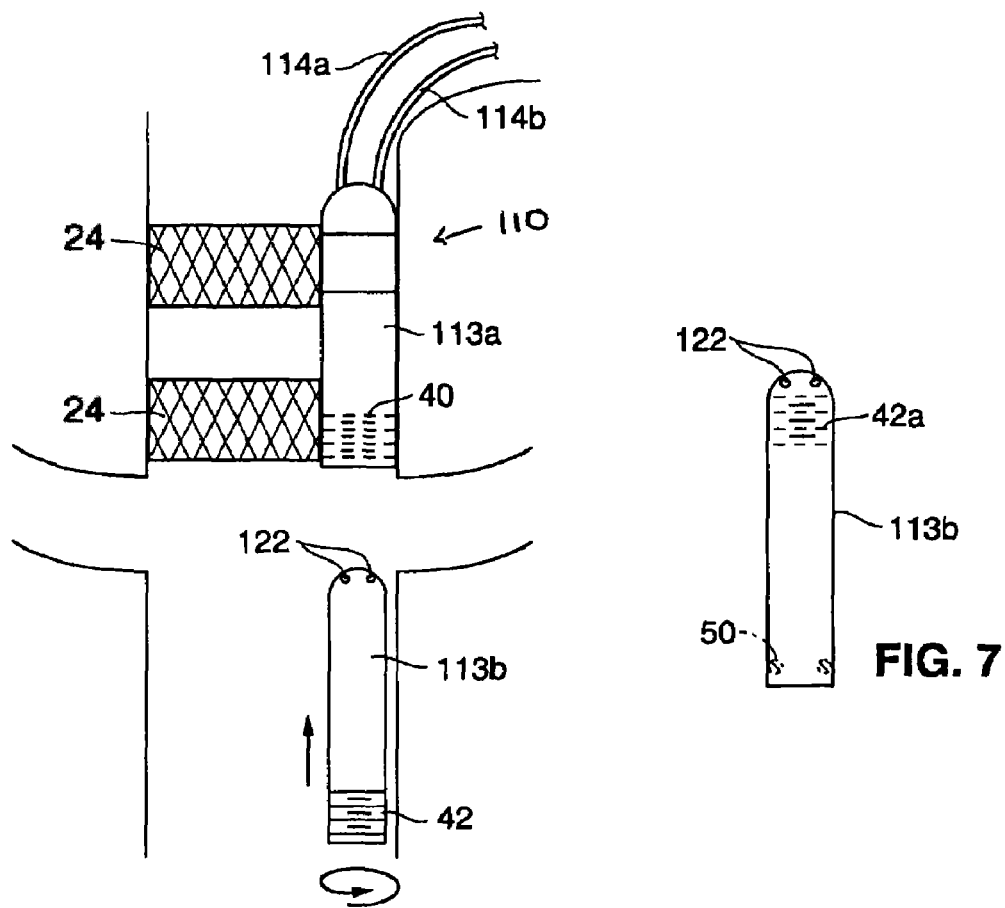
FIG. 6
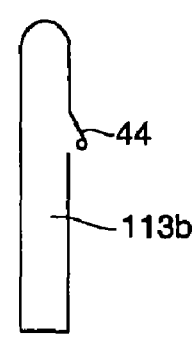
FIG. 7
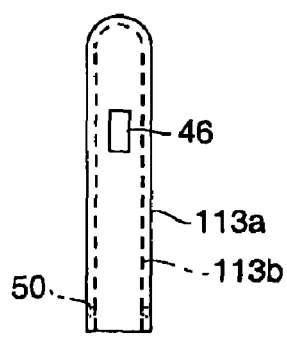 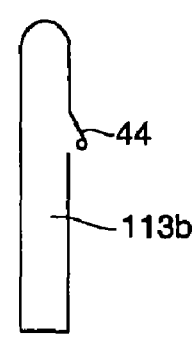 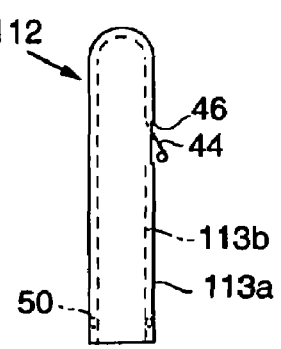
FIG. 8A  FIG. 8B  FIG. 8C ers for implantation of a pacemaker or ICD—thus delay-
IMPLANTABLE MEDICAL DEVICE HAVING PRE-IMPLANT EXOSKELETON

PRIORITY CLAIM

This application claims priority from prior Provisional Application Ser. No. 60/529,051, filed Dec. 12, 2003, and which is incorporated herein by reference.

FIELD OF THE INVENTION

The present invention generally relates to devices or systems implanted within the body for therapeutic and/or diagnostic purposes. In particular, the invention provides methods and devices for facilitating implantation of such systems within the patient's vasculature.

BACKGROUND OF THE INVENTION

Pacemakers, defibrillators and implanted cardioverter defibrillators ("ICDs") have been successfully implanted for years for treatment of heart rhythm conditions.

Pacemakers are implanted in patients who have bradycardia (slow heart rate). The pacemakers detect periods of bradycardia and deliver electrical stimuli to increase the heartbeat to an appropriate rate.

ICDs are implanted in patients who may suffer from episodes of fast and irregular heart rhythms called tachyarrhythmias. An ICD can cardiovert the heart by delivering electrical current directly to the heart to terminate an atrial or ventricular tachyarrhythmia, other than ventricular fibrillation. An ICD may alternatively defibrillate the heart in a patient who may suffer ventricular fibrillation (VF), a fast and irregular heart rhythm in the ventricles. During a VF episode, the heart quivers and can pump little or no blood to the body, potentially causing sudden death. An ICD implanted for correction of ventricular fibrillation will detect a VF episode and deliver an electrical shock to the heart to restore the heart's electrical coordination.

Another type of implantable defibrillation device treats patients who may suffer from atrial fibrillation (AF), which is a loss of electrical coordination in the heart's upper chambers (atria). During AF, blood in the atria may pool and clot, placing the patient at risk for stroke. An electrophysiological device implanted for correction of atrial fibrillation will detect an AF episode and deliver an electrical shock to the atria to restore electrical coordination.

Pacemakers and ICDs are routinely implanted in the pectoral region either under the skin (subcutaneous) or under the pectoral muscle. The leads are placed at appropriate locations around, within or on the heart. Because of this complexity, a cardiologist identifying a heart rhythm condition may be required to refer his or her patient to sub-specialists or surgeons for implantation of a pacemaker or ICD—thus delaying implantation of the device in a patient who urgently needs it. It is thus desirable to simplify these devices and the procedures for implanting them so as to permit their implantation by a broader range of physicians.

U.S. application Ser. Nos. 10/453,971 and 10/454,223 ("the '971 and '223 applications), filed Jun. 4, 2003, and Ser. No. 10/862,113, filed Jun. 4, 2004 (the '113 application) describe intravascular systems that may be used to deliver electrical energy to the heart such as for defibrillation, pacing, and/or cardioversion of the heart. Each of these applications is incorporated herein by reference for all purposes.

Generally speaking, the systems described in the '971, '113 and '223 applications include at least one housing containing the necessary circuitry and related components for delivering a charge to the heart for pacing, and/or defibrillation, etc. The systems may also include at least one electrode lead through which the electrical energy is delivered to the body. Some or all of these components are positioned within the vasculature, such as in the superior vena cava ("SVC"), the inferior vena cava ("IVC"), or the left or right subclavian, coronary sinus, and/or other vessels of the venous or arterial systems. For example, the housing containing electronics, circuitry, batteries, capacitors, etc. may be positioned in the IVC or SVC, while leads extending from the housing may extend to the left subclavian vein (LSV), the IVC, the coronary sinus of the heart, and/or the right ventricle of the heart. Retention devices may be used to retain some of these components within the vasculature.

The present disclosure describes components that facilitate implantation and later removal of the housing containing electronics, circuitry, batteries, etc. in an intravascular system. In particular, the application describes a sleeve or "exoskeleton" that is implanted in the vasculature. The exoskeleton may be retained in place using a retention device. Following implantation of the exoskeleton, the housing is inserted into the exoskeleton. If at some date it becomes necessary to explant the housing, it may be withdrawn from the exoskeleton and removed from the body, leaving the exoskeleton in place.

BRIEF DESCRIPTION OF THE DRAWINGS

FIG. 3C is a plan view of an insert positioned within an exoskeleton, showing a third arrangement of electrical contacts.

FIG. 4A is a plan view of an insert.

FIG. 4B is a plan view of a distal portion of an exoskeleton assembled with an insert. The exoskeleton is shown in cross-section.

FIG. 6 is an elevation view showing an alternative embodiment of an exoskeleton and insert.

FIG. 7 is a side elevation of an alternative insert.

FIG. 8A is a front elevation view showing an alternative exoskeleton.

FIG. 8B is a side elevation view showing an alternative insert for use with the exoskeleton of FIG. 8A.

FIG. 8C is a side elevation view showing the components of FIGS. 8A and 8B in assembled form.

DETAILED DESCRIPTION OF THE DRAWINGS

Cardiac Anatomy

Figure 1:
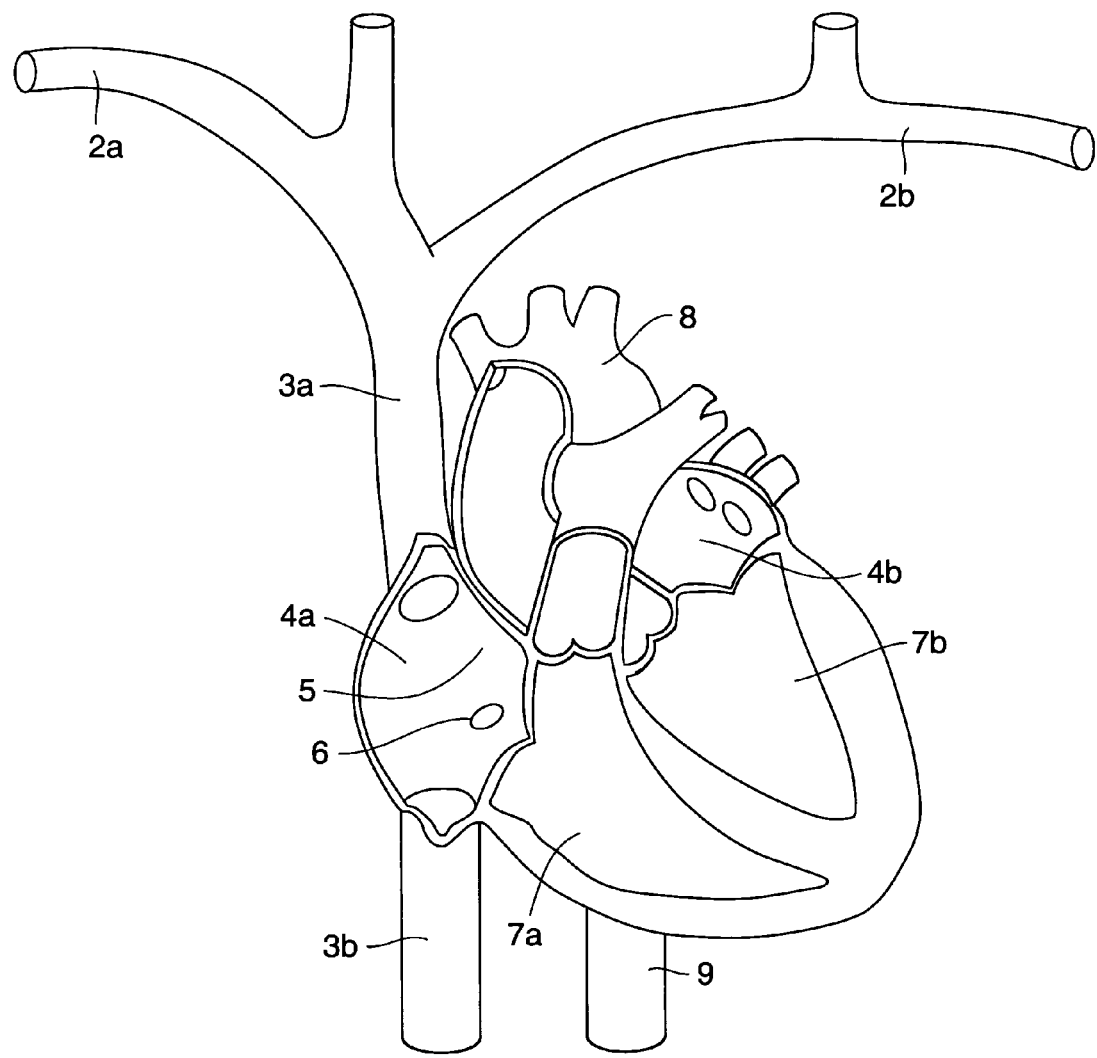
FIG. 1 is a perspective illustration showing human cardiac anatomy.

FIG. 1 shows the cardiac anatomy of a human, including the heart and major vessels. The following anatomic locations are shown and identified by the listed reference numerals:

| | |
|---|---|
| Right Subclavian | 2a |
| Left Subclavian | 2b |
| Superior Vena Cava (SVC) | 3a |
| Inferior Vena Cava (IVC) | 3b |
| Right Atrium (RA) | 4a |
| Left Atrium (LA) | 4b |
| Right Atrial Appendage (RAA) | 5 |
| Coronary Sinus Ostium (CS Os) | 6 |
| Right Ventricle (RV) | 7a |
| Left Ventricle (LV) | 7b |
| Aortic Arch | 8 |
| Descending Aorta | 9 |

Exoskeleton configurations will be described in the context of an intravascular system useful for electrophysiological ("EP") applications (such as implantable defibrillation systems and associated components), it should be appreciated that the disclosed embodiments and methods or variations thereof may be used to implant other types of intravascular systems, including but not limited to pacing, defibrillation or cardioversion systems. The components may find further use in connection with intravascular systems for delivering other forms of therapy (e.g., pharmaceutical therapies) to the body.

Such systems are described in U.S. Provisional Application No. 60/634,585, INTRAVASCULAR DELIVERY SYSTEM FOR THERAPEUTIC AGENTS, filed Dec. 9, 2004, the entirety of which is incorporated herein by reference. Other systems for which the exoskeleton components may be useful include intravascular diagnostic systems such as those that monitor blood glucose, blood oxygen, or other parameters. It should also be mentioned that although this application describes the systems for use in the vasculature, pre-implant exoskeletons may be implanted at other sites within the body where medical implants are to be placed. For example, exoskeletons may function as pre-implant devices in subcutaneous pockets or in organs or body cavities throughout the body.

General Discussion

Figure 2:
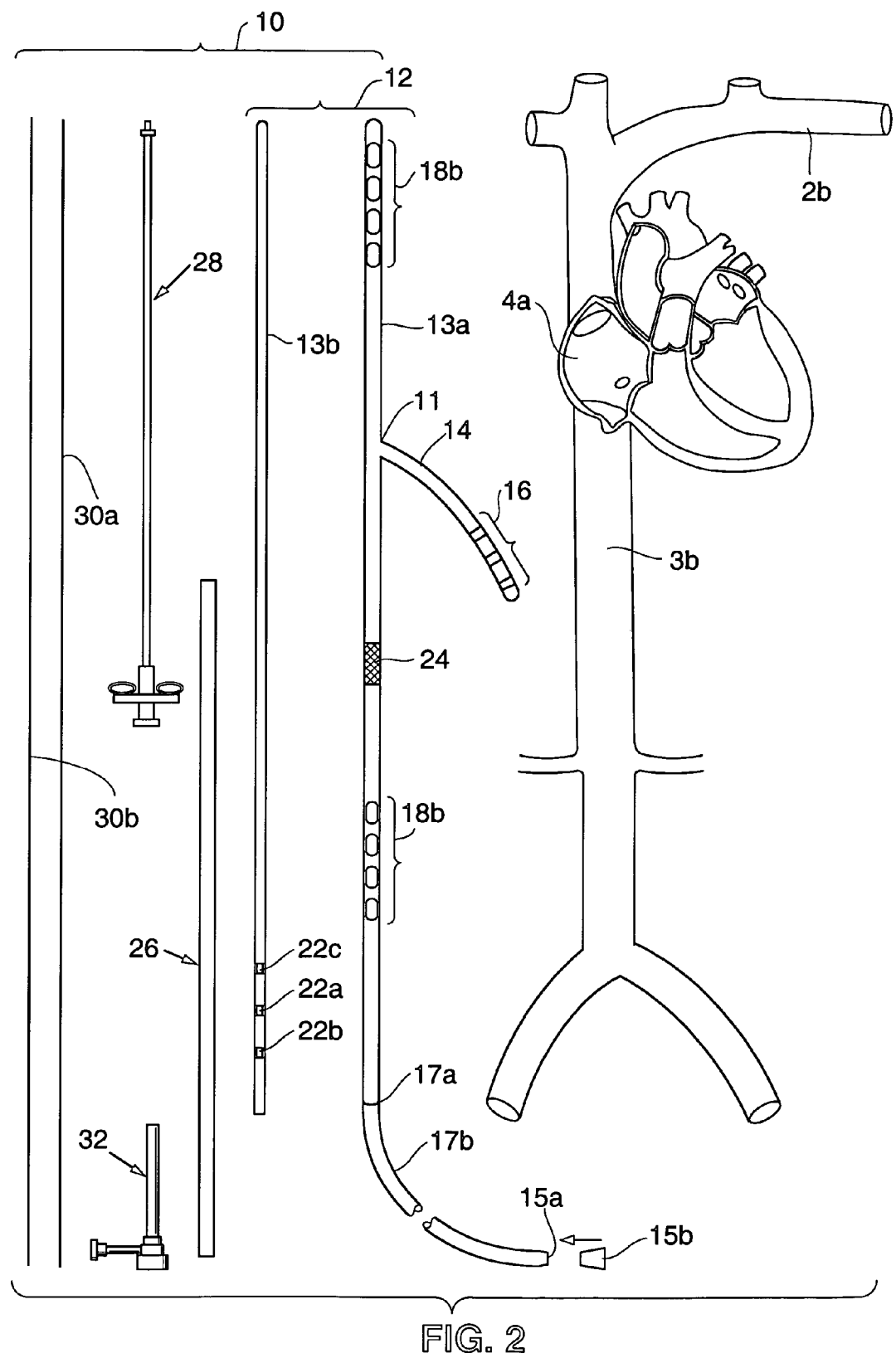
FIG. 2 is a plan view generally showing components of a first embodiment of intravascular defibrillation and/or pacing system and associated implantation tools.

FIG. 2 generally shows one example of an intravascular defibrillation system 10 of a type that may utilize components of the type described herein. The elements of system 10 include a defibrillation and/or pacing device 12, which is comprised of a tubular exoskeleton 13a and an insert 13b that is slidably received within an opening 15a in the exoskeleton. Exoskeleton 13a may function as a "pre-implant", i.e., a sleeve or shell that is first anchored within a vessel, whereas insert 13b serves to house the electronics and associated features for carrying out the system functions.

The exoskeleton 13a is proportioned to be passed into the vasculature and to be anchored within the patient's vasculature with minimal obstruction to blood flow. Suitable sites for the exoskeleton may include, but are not limited to the venous system using access through the right or left femoral vein or the subclavian or brachiocephalic veins, or the arterial system using access through one of the femoral arteries. Thus, the exoskeleton preferably has a streamlined maximum cross sectional diameter which may be in the range of 3-15 mm or less, with a most preferred maximum cross-sectional diameter of 3-8 mm or less. The cross-sectional area of the exoskeleton in the transverse direction (i.e., transecting the longitudinal axis) should be as small as possible while still accommodating the required components within the insert 13b. This area is preferably in the range of approximately 79 $mm^2$ or less, and more preferably in the range of approximately 40 $mm^2$ or less, or most preferably between 12.5-40 $mm^2$.

The exoskeleton preferably forms a fluid-tight barrier against migration of body fluids into its interior. Avoiding leakage of blood and body fluids avoids thrombus formation and endothelial or cellular growth within the exoskeleton and onto the insert, and thus allows the insert to be removed from the exoskeleton when necessary for replacement or servicing. Examples of materials useful for the exoskeleton include PTFE, ePTFE, PFPE, other fluropolymers, polyurethanes, silicone, polyolefin rubber, dacron polyester, PET, PMMA, EVA or polypropylene, ceramics, surface reactive glass ceramics (including bioglasses or bioceramics), or metals including titanium and its alloys and/or other biocompatible metals. Exoskeleton 13a may be formed of a polymeric material having a reinforcing structure (e.g., a metallic or polymeric braid) over, under or integrated with the polymeric material. One example of this type of arrangement would be a braid lined with a Teflon polymer.

Because the exoskeleton might remain permanently in the vasculature, it may be desirable to promote tissue growth (e.g., cellular encapsulation, in-growth, endothelialization) onto and/or into the exoskeleton 13a. Tissue growth onto/into the exoskeleton can improve the stability of the exoskeleton within the vessel, and may improve the biocompatibility of the system within the vessel by improving blood-surface compatibility. Cellular growth may be encouraged by giving the exoskeleton an in-growth promoting surface using structural features. For example, all or a portion of the exterior surface of the exoskeleton may have pores (e.g., from a porous material), interstices (e.g., in a mesh material), or other surface modifications into or onto which cellular growth can occur. In one embodiment, the exoskeleton may have an exterior surface formed or covered by Dacron or by a form of ePTFE having a node to fibril length of approximately 15-25 microns. Cellular growth into or onto the exoskeleton may also be promoted using a substance that promotes in-growth. For example, the exoskeleton may be coated or impregnated with a substance such as albumen, growth factors, synthetic or natural therapeutic molecules, or any other substance that will promote cellular growth.

On the other hand, if the option to explant the exoskeleton is desired, it may be formed of a material or covered by a layer or coating having anti-proliferative properties so as to minimize endothelialization or cellular ingrowth, since minimizing growth into or onto the device will help minimize vascular trauma when the device is explanted. A form of ePTFE having a note-to-fibril length of approximately 1-10 microns, and preferably less than approximately 10 microns, may be used for this purpose.

In another embodiment, the exoskeleton may be constructed such that it will degrade over a period of time calculated such that degradation will occur after the intended useful life of the insert. Materials suitable for this purpose include LPLA, polyglycolic acid, polydioxanone, polyanhydrides or other erodable materials. According to this embodiment, degradation of the exoskeleton would preferably be timed to occur following removal of the implant.

The exoskeleton surface may also be anti-thrombogenic (e.g., using materials or coating such as perfluorocarbon coatings applied using supercritical carbon dioxide), although if cellular ingrowth is desired some thrombosis may be allowed as a substrate for endothelial growth. The exoskeleton may also include a surface or coating, which elutes compositions, such as anti-thrombogenic compositions (e.g., heparin sulfate) and/or anti-proliferative compositions and/or immunosuppressive agents.

Referring to FIG. 2, the most proximal section of the device may include a transition 17a to a more flexible tail section 17b of the exoskeleton, which may be coiled and tucked into a subcutaneous pocket following implantation as will be discussed below.

In another embodiment, the insert 13b may fit snugly into the exoskeleton 13a, in which case the exoskeleton may function as a coating on the insert 13b.

One or more electrode leads 14 may extend as branches from the exoskeleton 13a. Leads include electrodes 16 for delivering electrical energy to the surrounding body tissue. In the FIG. 2 embodiment, the lead 14 may be positionable within the right ventricle (RV) of the heart. Additional electrodes may be positioned on the body of the exoskeleton. For example, the exoskeleton may include electrodes 18a positionable within the left subclavian vein (LSV) 2b, and electrodes 18b positionable within the inferior vena cava (IVC) 3b.

It should be noted that the term "exoskeleton" is not intended to mean that the exoskeleton 13a is necessarily hard or rigid. As discussed, the exoskeleton preferably forms a barrier against migration of body fluids into contact with the insert, but it need not be a rigid barrier. In a preferred embodiment the exoskeleton is sufficiently flexible to be passed through the vasculature. However, certain sections of the exoskeleton 13a may include additional features that supplement the strength and stability of those sections after they have been positioned at their final location within the vasculature. This may be desirable during removal of the insert 13b from the exoskeleton 13a to assist the exoskeleton 13a in resisting axial forces applied against it during withdrawal of the insert.

For example, in the FIG. 2 embodiment it may be desirable to reinforce the lead 14 or the portion of the exoskeleton positioned distally of lead bifurcation 11. One reinforcement method might include providing the exoskeleton with pockets of curable or reactive polymer in a liquid state. These pockets might be positioned throughout the exoskeleton, or at select regions such as the lead 14, and/or the bifurcation 11, and points distal to the bifurcation 11. Once the exoskeleton is positioned or just prior to extraction of the insert, the polymer would be cured using the appropriate curing method (e.g., UV exposure, chemical contact, thermal activation, etc.). The cured material can help the exoskeleton to retain a desired shape within the vessel, and can assist with axial stability. Another embodiment of a reinforcement method might involve inserting reinforcing wires or ribbons through lumens in the sidewalls of the exoskeleton following implantation of the exoskeleton or just prior to extraction of the insert.

Figure 3A:
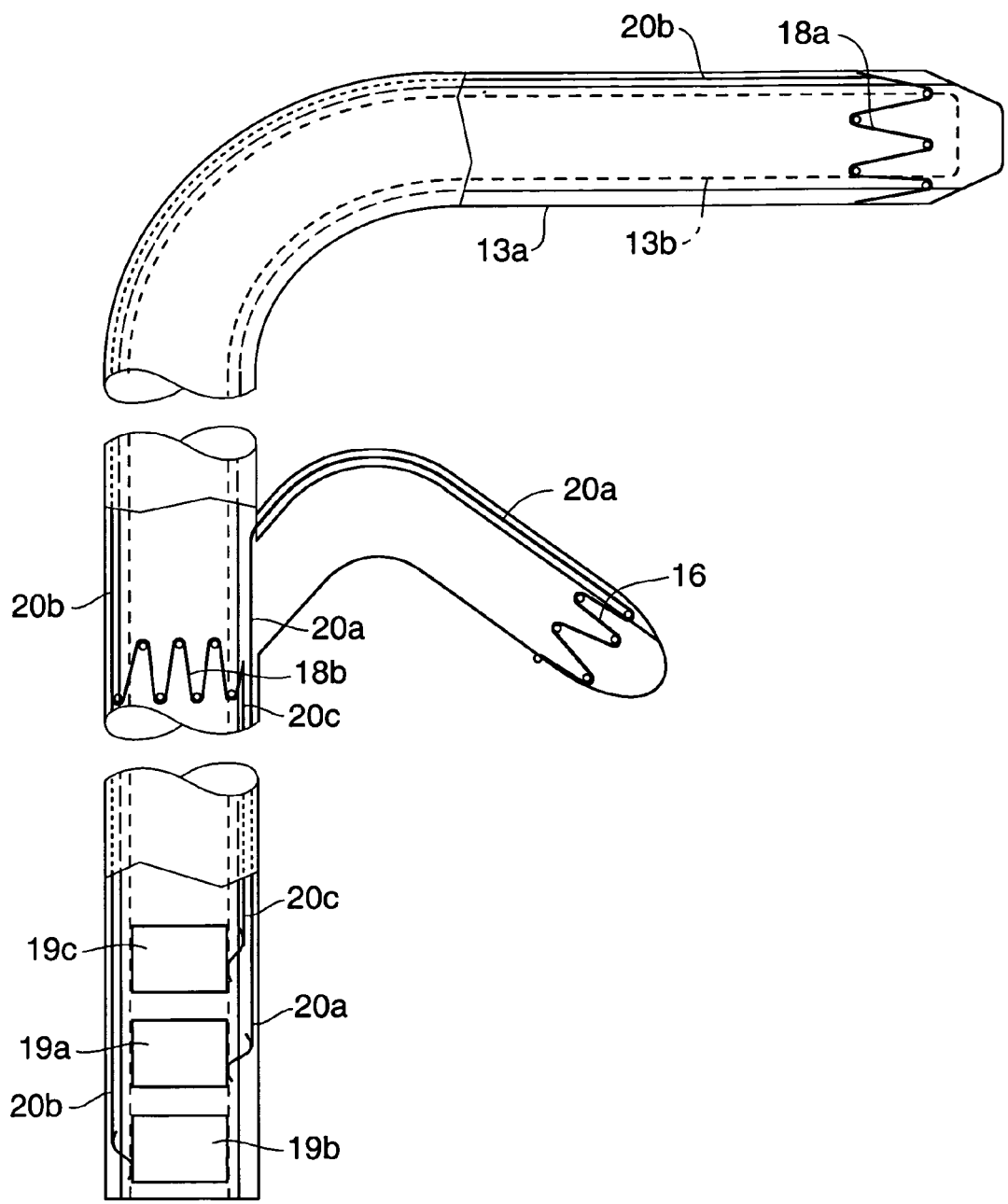
FIG. 3A is a plan view of a distal portion of the exoskeleton of FIG. 2.

Referring to FIG. 3A, the interior surface of the exoskeleton includes a plurality of electrical contacts 19a, b, c. Each of the contacts 19a, 19b, 19c is connected to a corresponding wire 20a, 20b, 20c that extends through the exoskeleton (e.g., through the main lumen or though channels in the sidewalls of the exoskeleton). Each wire is in turn coupled to one of the electrodes or electrode arrays 16, 18a, 18b. FIG. 3A also illustrates an alternative form of electrodes that differ from the surface electrodes shown on the FIG. 2 embodiment. In the FIG. 3A embodiment, each wire (e.g., wire 20a) extending through the exoskeleton penetrates the wall of the exoskeleton and is wound on the surface of the exoskeleton to form the electrode. Sealing compound is preferably used to seal the exoskeleton at the point of penetration.

Referring again to FIG. 2, the insert 13b is a hermetically sealed housing containing electronics and other features necessary for the operation of the system. These features may include one or more pulse generators, including associated batteries, capacitors, microprocessors, and circuitry for generating defibrillation pulses. Detection circuitry for detecting arrhythmias or other abnormal activity of the heart may also be housed within insert 13b. The housing may be made from metals such as titanium or titanium alloys, polymers, or other suitable materials. Although the exoskeleton will preferably isolate the insert from body materials, the insert may be covered by a layer or coating having anti-proliferative properties so as to minimize endothelialization or cellular ingrowth onto the insert in the event some fluids migrate into the exoskeleton.

One or more electrical contacts 22a, 22b, 22c are positioned on the exterior surface of the insert 13b. The contacts 22a, 22b, 22c may take the form of conductive elements attached to the housing of the device insert. Alternatively, if the insert 13b includes a conductive housing to which an insulating material is to be applied, the contacts may be formed by selectively applying the coating or removing portions of the coating to leave one or more exposed contact regions on the surface of the insert.

Contacts 22a, 22b, 22c are positioned to electrically couple to the corresponding contacts 19a, 19b, 19c (FIG. 3A) inside the exoskeleton when the device 12 is fully When the contacts are properly coupled, electrical energy emitted by the pulse generator within the housing is directed to the appropriate electrodes 16, 18a, 18b on the exoskeleton. Likewise, any electrodes are positioned to detect the heart's electrical activity, are electrically coupled to detection circuitry within the insert 13b.

Figure 3B:
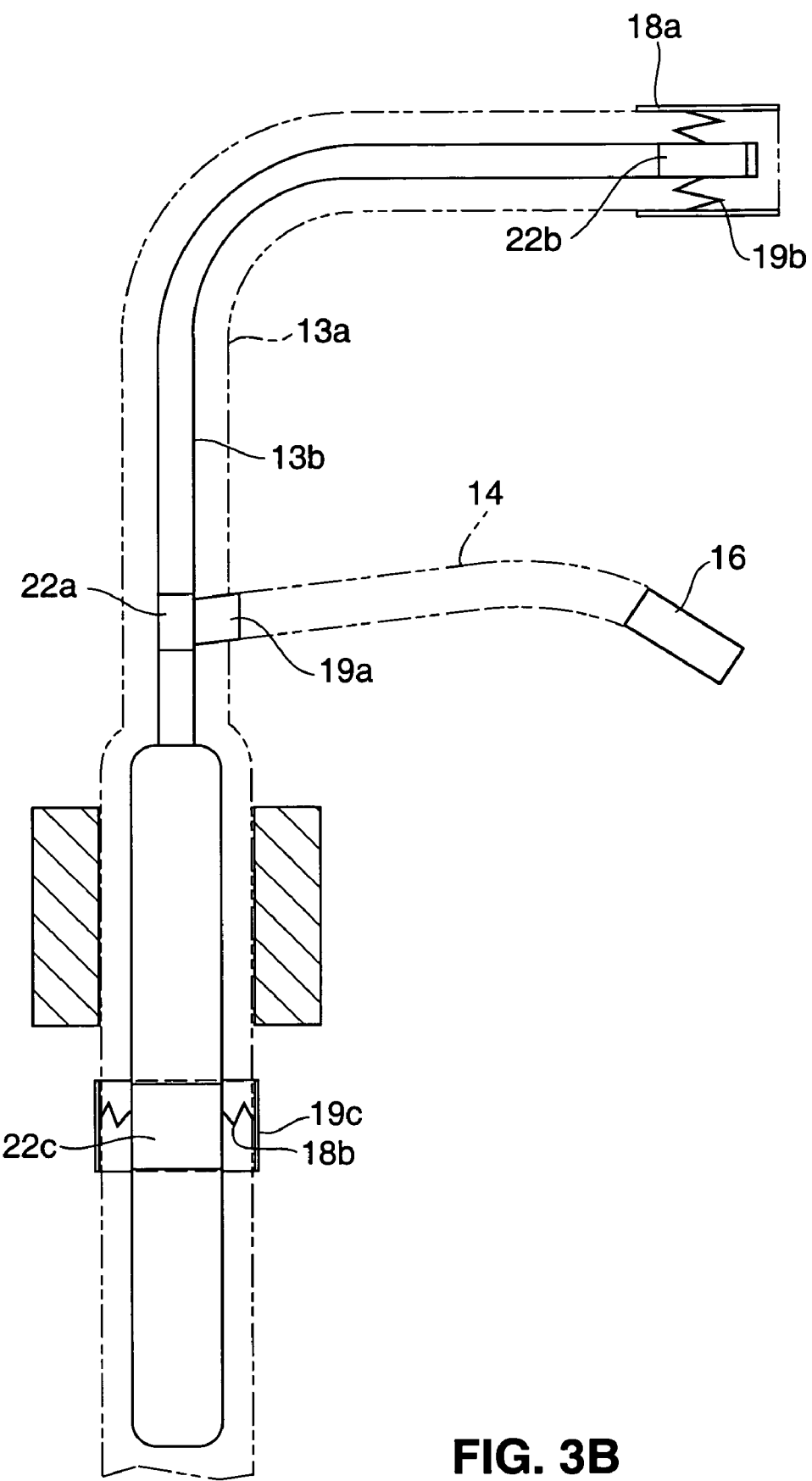
FIG. 3B is a plan view of the exoskeleton and insert of FIG. 2, showing an alternative arrangement of electrical contacts.

FIG. 3B illustrates alternative positioning of the contacts 19a, b, c and the contacts 22a, 22b, 22c. Rather than positioning all contacts within a cluster towards the proximal end of the device 12 as shown in FIG. 3A, the FIG. 3B embodiment positions contacts 19b, 22b in the region of the LSV electrode 18a, and contacts 19c, 22c in the region of the IVC electrode 18b. The contacts 19a, 22a for the RV electrode 16 are positioned near the bifurcation of the lead 14.

Returning again to FIG. 3A, it should be noted that if the contacts 19a, b, c are positioned in a proximal portion of the exoskeleton 13a, the insert 13b need not be proportioned to extend to the distal end of the exoskeleton. However, the insert 13b may be long enough to extend to the distal end even if it not necessary for making electrical contact.

Another arrangement of contacts is shown in FIG. 3C, which illustrates the distal portion of insert 13b disposed within the distal portion of exoskeleton 13b. The walls of the exoskeleton are shown in cross-section to allow the insert to be seen. As shown, a tiered structure is used for the distal portions of the insert and exoskeleton with conductive rings forming contacts 19e, 22e at each tier 7. More specifically, at each tier 7 a conductive ring 19e lines the interior surface of the exoskeleton 13b, and a corresponding conductive ring 22e lines the exterior surface of the insert 13a. The tiers may be proportioned such to create an interference fit between the insert and the exoskeleton.

The system may include alternative features that engage the insert 13b within the exoskeleton 13a. The retention forces between the exoskeleton and insert are preferably sufficient to retain the insert, but also such that they may be overcome by manually withdrawing the insert 13b. As one example, the interior surface of the exoskeleton and/or the exterior surface of the insert may include raised elements (e.g., rib features, broadened sections etc.) that cause the two components to engage due to friction forces between adjacent surfaces. FIG. 4A illustrates raised elements 23 on the surface of the insert 13b. Alternatively, the general fit between the components 13a, 13b may be sufficient to create such friction.

As another example, one or more of the contacts within the exoskeleton 13a may take the form of a metallic leaf spring radially biased towards the central axis of the exoskeleton. This is illustrated in FIG. 4B. In this embodiment, the contacts 19b are inwardly biased leaf springs. The electrodes 18a may be strips of conductive material or sections of conductive tubing electrically coupled to the contacts 22b using rivets 21 or other conductive elements passing through the wall of the exoskeleton. As shown, when the insert is placed within the exoskeleton, leaf spring contact 19b springs into engagement with a corresponding contact 22b on the insert 13b. To facilitate engagement, the contact 22b may be positioned within a recess formed in the surface of the insert 13b as shown. A plurality of similar leaf springs (which may or may not be conductive) may be used at one or more locations on the exoskeleton surface to ensure that engagement between the components is secure.

Figure 10A:
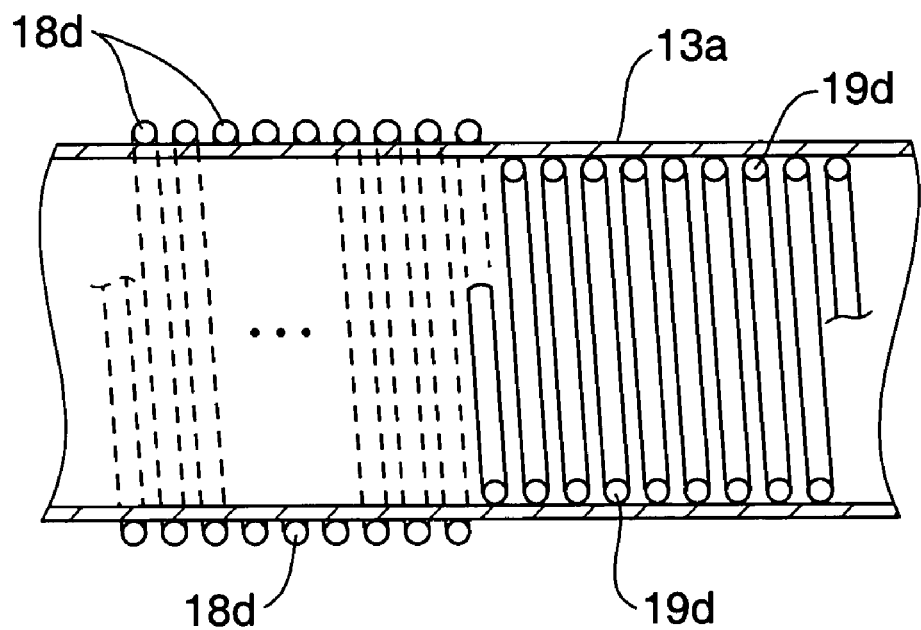
FIGS. 10A and 10B illustrate various electrode and contact embodiments useful for exoskeletons.
Figure 10B:
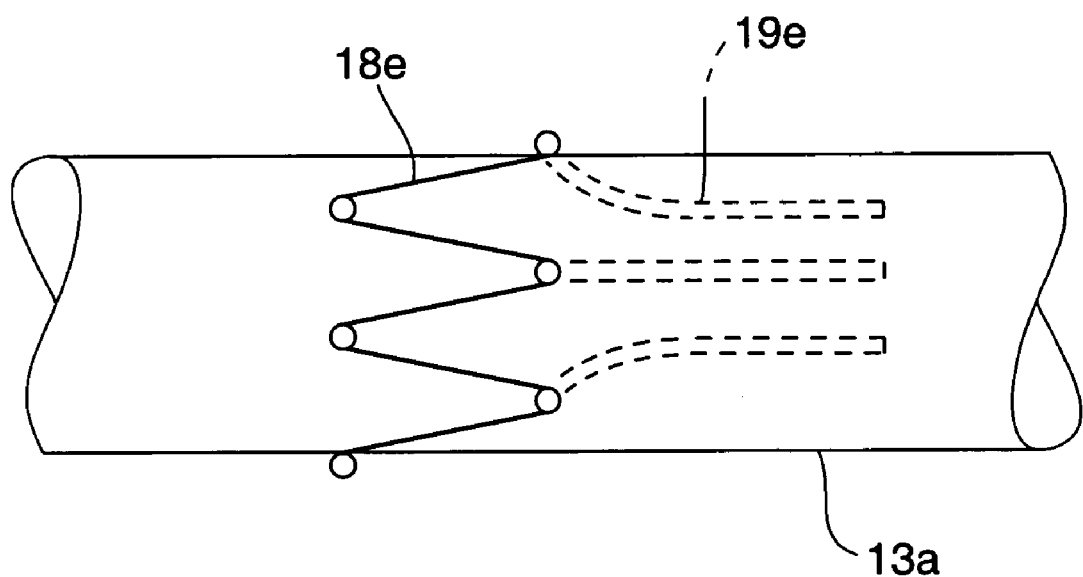

Some alternative electrode and contact designs similar to the FIG. 3A design are shown in FIGS. 10A and 10B. It should be mentioned that the configurations for the electrodes and associated contacts described in this application are merely examples and not given as an all-inclusive list.

In one embodiment shown in FIG. 10A, an electrode 18d comprises a wire coil, wherein a first portion of the coil is positioned within the exoskeleton to form a contact 19d that makes contact with a corresponding contact on the insert. A second portion of the coil is wrapped around the exterior surface of the exoskeleton for contact with tissue.

In a similar embodiment, shown in FIG. 10B, the electrode 18e is formed of a strand wire wound in an undulating pattern. A portion of the pattern is positioned inside the exoskeleton to serve as contact 19e, whereas another portion extends through the exoskeleton wall to form the external electrode. A similar pattern may be cut into a sheet or tube of metal rather than looped using a wire. The contact portion 19e of the wire may be biased inwardly in a manner similar to the leaf springs 19b of FIG. 4B.

Referring again to FIG. 2, one or more retention devices such as anchor 24 are provided for retaining the exoskeleton within a blood vessel. Anchor 24 includes structural features that allow the anchor to self-expand into radial engagement with a vessel wall. For example, a band, mesh or other framework formed of one or more shape memory (e.g., nickel titanium alloy, nitinol, thermally activated shape-memory material, or shape memory polymer) elements or stainless steel, Elgiloy, or MP35N elements may be used. In this embodiment the anchor 24 is preferably constructed to promote tissue ingrowth to as to enhance anchor stability within the vessel. Structural features such as mesh or other framework configurations are suitable for this purpose, although compositions and/or coatings that promote in-growth may also be used.

During implantation, a retractable sheath 26 may be slidably positioned over the anchor 24 and the exoskeleton 13a so as to retain the anchor in its compressed position. (The sheath 26 may also be used to hold the lead branch 14 streamlined against the exoskeleton 13a during implantation.) Retraction of the sheath once the exoskeleton is properly positioned allows the anchor 24 to expand into contact with the surrounding walls of the vessel, thereby holding the exoskeleton in the desired location. Once deployed, the anchor 24 is preferably intimate to the vessel wall, which is distended slightly, allowing the vessel lumen to remain approximately continuous despite the presence of the anchor and thus minimizing turbulence or flow obstruction. Although self-expansion of the anchor is preferable, mechanical expansion means (e.g., balloon expanders etc) may be used for active expansion of the anchor.

The anchor may also have drug delivery capability via a coating matrix impregnated with one or more pharmaceutical agents.

The anchor 24 may be configured such that the exoskeleton 13a and anchor 24 share a longitudinal axis, or such that the axes of the exoskeleton 13a and anchor 24 are longitudinally offset.

An implantation mandrel 28 is attachable to the proximal end of exoskeleton 13a (e.g., at transition region 17a) for advancing the exoskeleton into position within the body. The mandrel 28 may also be used to push the insert into the exoskeleton or a separate tool can be used for this purpose. The system may additionally be provided with other components useful for implanting the system, including guidewires 30a, 30b and an introducer 32. If guidewires are to be used for implantation of the exoskeleton, the exoskeleton will preferably include guidewire lumens that permit tracking of the exoskeleton over the guidewires, or openings formed at the distal end of the exoskeleton and/or lead 14 for receiving the guidewires. The distal openings would preferably include seals to prevent migration of blood or other body fluids into the exoskeleton. The openings might instead include one-way valves that allow any body fluids that pass into the exoskeleton to be purged from the exoskeleton using a fluid (e.g., saline or carbon dioxide gas) injected into the proximal opening 15.

FIGS. 5A through 5E illustrate implantation of the system 10 of FIG. 2. In the illustrated method, the exoskeleton is implanted first, and then the insert is passed into the exoskeleton. However, in an alternative implantation method the insert may be passed into the exoskeleton outside the body and the two components introduced simultaneously.

A small incision is first formed in the femoral vein and the introducer sheath 32 is inserted through the incision into the vein to keep the incision open during the procedure. Next, guidewires 30a, 30b are passed through the sheath 32 and into the inferior vena cava 3b. Guidewire 30a is steered under fluoroscopy into the left subclavian vein 2b and guidewire 30b is guided into the right ventricle 7a of the heart. In an alternative embodiment of the implantation, only guidewire 30b is used and is advanced into the right ventricle 7a.

Next, the lead 14 (FIG. 2) is threaded over guidewire 30b by extending the guidewire into the exoskeleton and out of the exoskeleton via an opening in the lead 14. If both guidewires are used, the distal end of the exoskeleton 3b is threaded over guidewire 30a. The lead 14 and the distal end of the exoskeleton 13a are then passed through the introducer sheath 32 and into the IVC 3b. See FIG. 5A. Pushing on the exoskeleton causes the lead 14 to track over guidewire 30b while the exoskeleton advances within the vasculature (and over guidewire 30b if used).

The guidewires 30a, 30b are withdrawn. If necessary, a fluid such as saline or CO2 is directed through exoskeleton as described above to purge any body fluids from the exoskeleton.

Figure 5A:
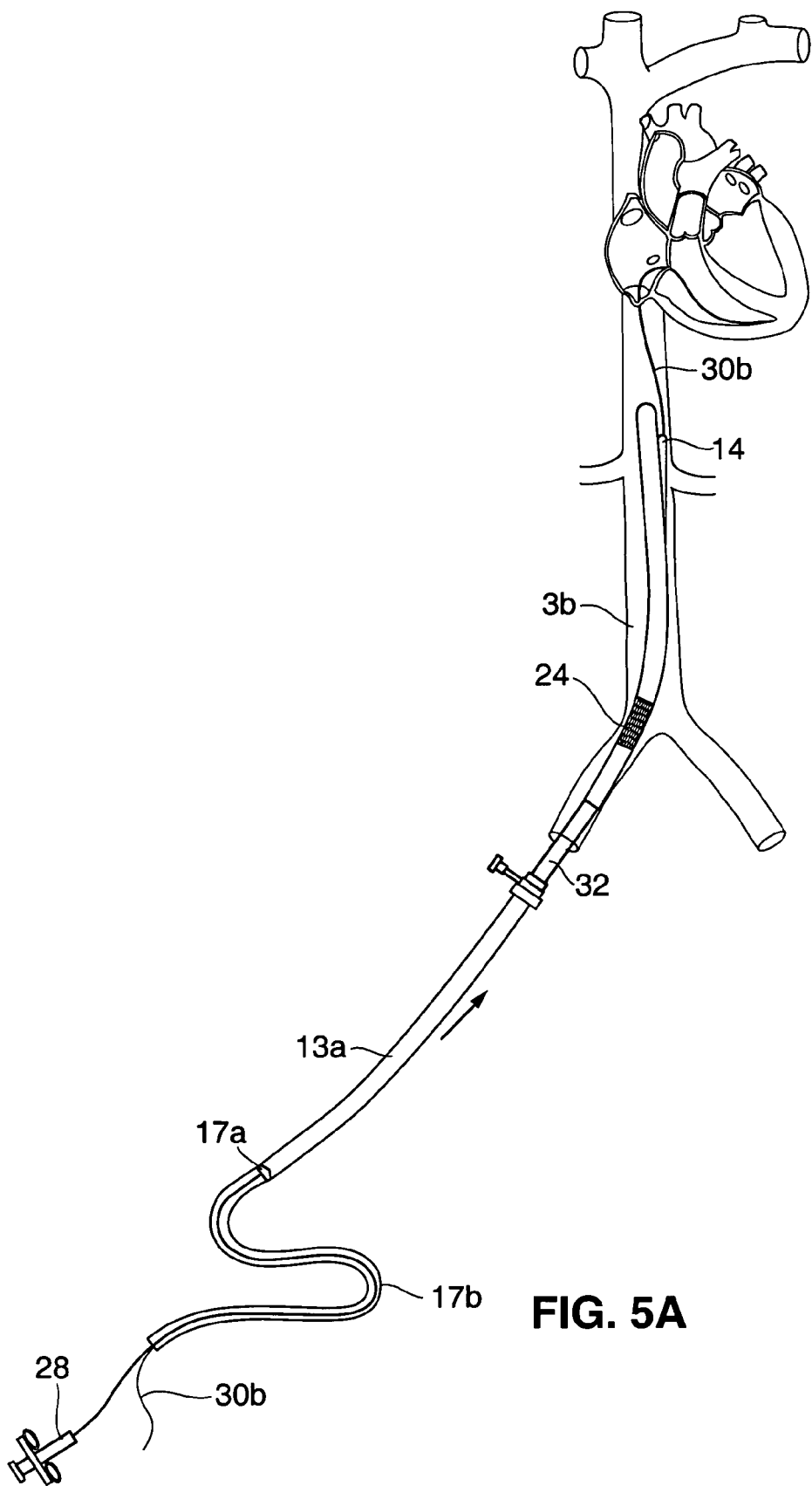
FIGS. 5A through 5E are a sequence of schematic views of a heart and associated vasculature, illustrating an implantation method using the system of FIG. 2.
Figures 5B, 5C:
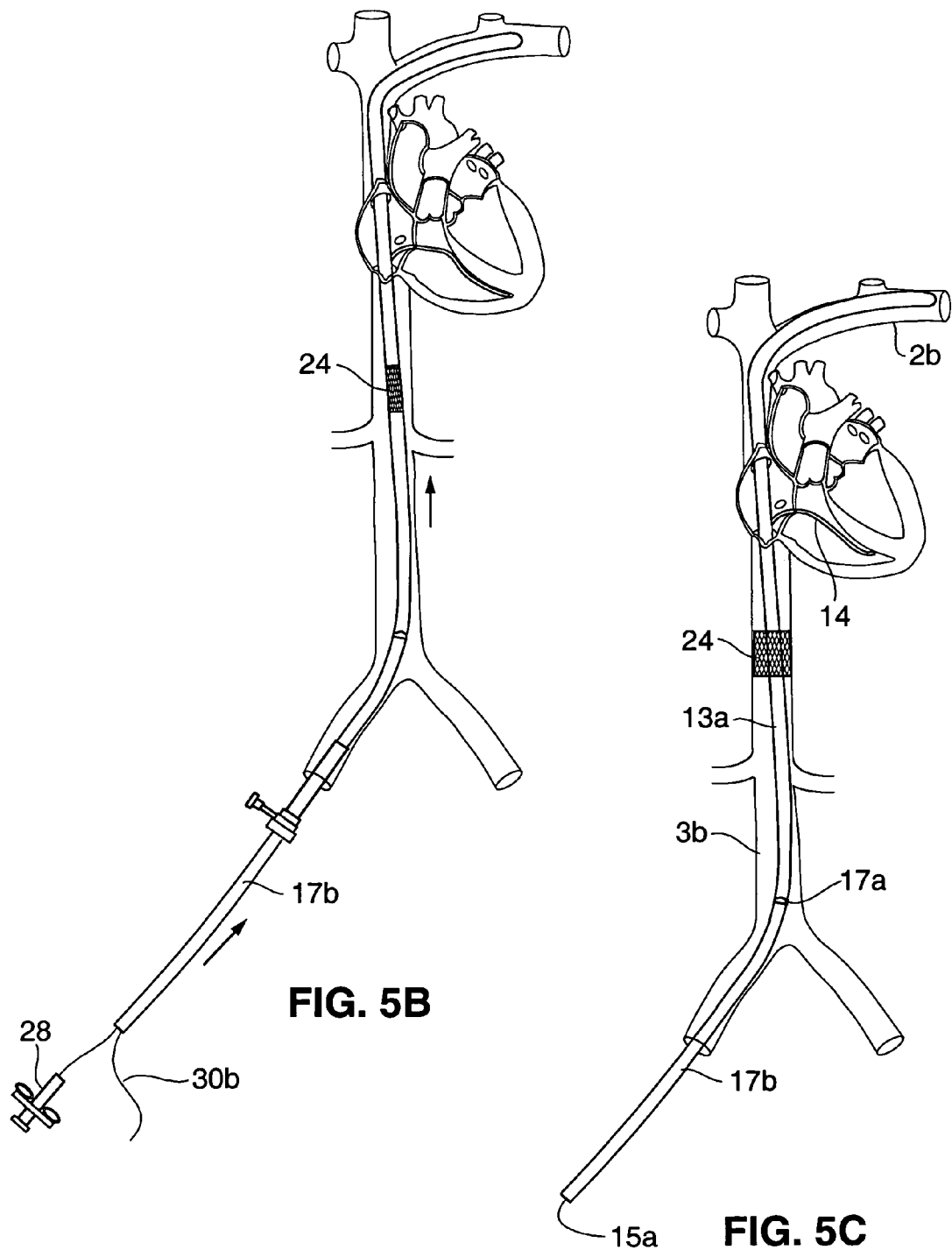

Next, implantation mandrel 28 is attached to the proximal portion of the exoskeleton 13a (e.g., at transition region 17a) and is used to push the exoskeleton further into the vasculature. Advancement of the mandrel 28 is continued until the distal portion of the exoskeleton reaches the desired position within the LSV 2*b*, and the lead 14 had tracked the guidewire 30*b* into the right ventricle 7*a* as shown in FIG. 5B. At this stage, some of the flexible tail section 17*b* of the exoskeleton remains outside the body.

The exoskeleton is next anchored in place by releasing the anchor 24 to its expanded position as shown in FIG. 5C. The anchor expands into contact with the surrounding vessel wall, thereby preventing migration of the exoskeleton. If desired, the distal portion of exoskeleton 13*a* may be anchored in the LSV 2*b* using another suitable anchor. The mandrel 28 is detached from the exoskeleton and withdrawn from the body.

Figure 5D:
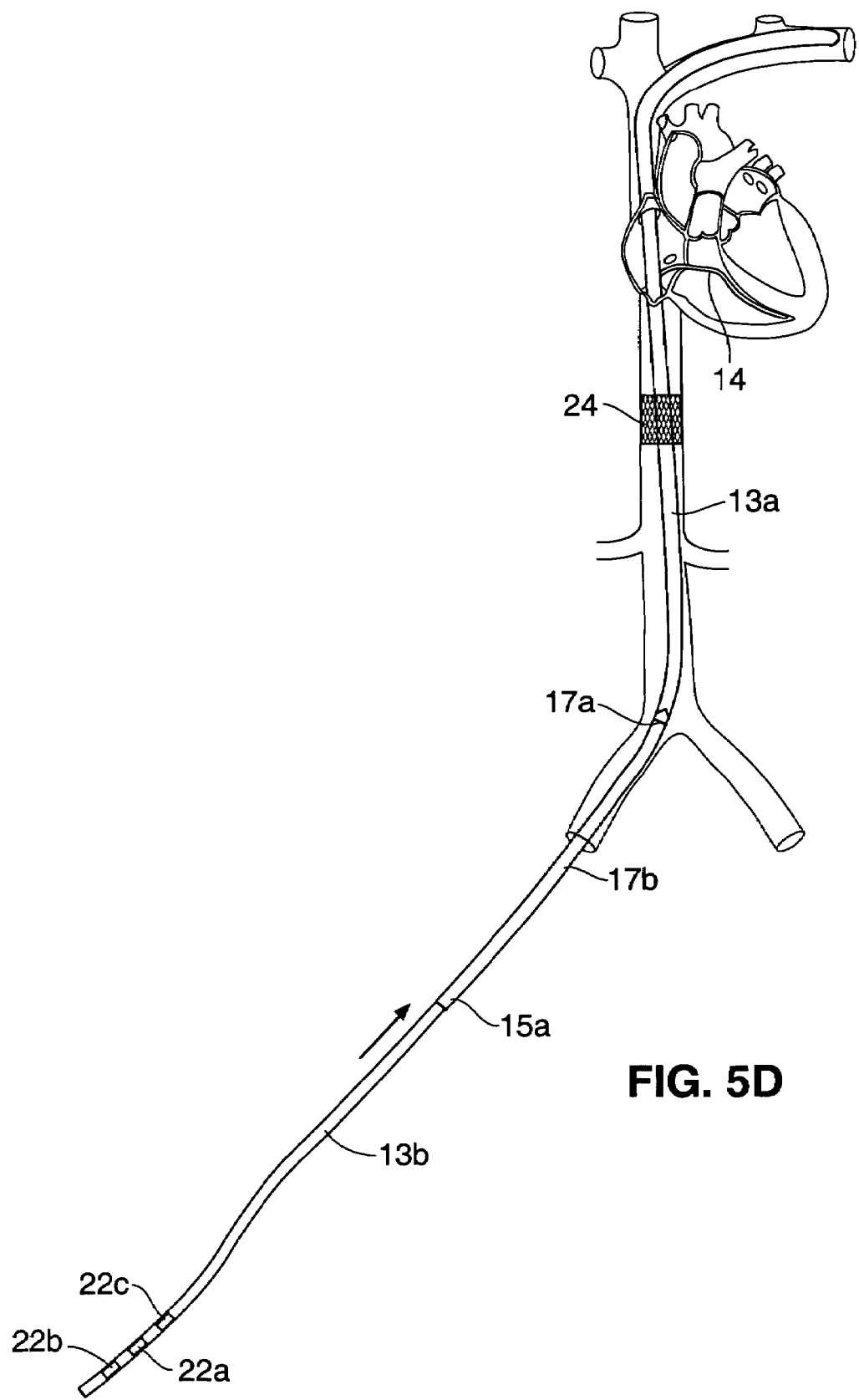
Figure 5E:
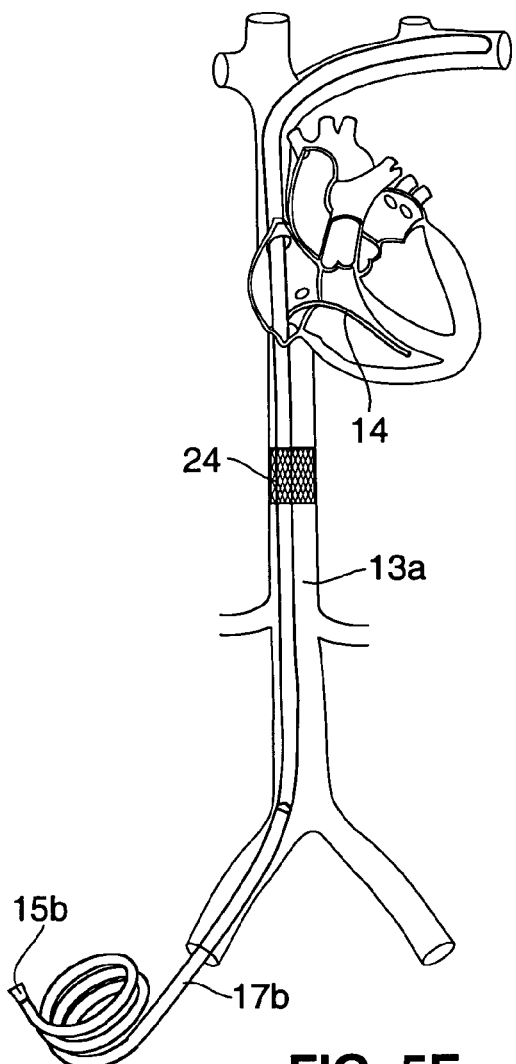

Next, the insert 13*b* is inserted into the exoskeleton as shown in FIG. 5D. If necessary, the implantation mandrel 28 may be attached to the insert 13*b* and used to push the insert 13*b* into position. The insert 13*b* is advanced to a point at which the contacts on the insert 13*b* have made electrical contact with the corresponding contacts of the exoskeleton. Finally, the mandrel 28 is removed and the opening 15*a* in exoskeleton is sealed using a cap or plug 15*b*, or using a sealing compound that will harden to seal the opening 15*a*. The flexible tail section 17*b* of the exoskeleton is coiled and tucked into the femoral vein or into a subcutaneous pocket adjacent to the femoral vein and is stored there for future access. The incision through the patient's skin is preferably closed and allowed to heal.

Future access to the insert 13*b* may be needed for a variety of reasons. For example, if the battery within the insert 13*b* should become depleted, the insert may be removed and replaced with a new device, or a charging device may be coupled to the insert 13*b*.

If the insert is to be replaced, a femoral incision is formed to gain access to the tail section 17*b*. A sufficient length of the tail 17*b* is removed from the body to permit access to the opening 15*a* in the tail 17*b*. The opening 15*a* is unsealed such as by removing its cap, plug 15*b* or seal. Alternatively, the exoskeleton may be re-opened by snipping off the proximal portion of the tail within which the cap, plug or seal is positioned. An extraction tool such as mandrel 28 may be passed into the exoskeleton and used to engage the insert. To facilitate this process, an alternative mandrel may be used that includes a distal coupling comprising a mouth that is significantly broader than the proximal end of the device. When the mandrel is advanced through the exoskeleton towards the insert 13*b*, the mouth will pass over the proximal end of the device 10 and will then be actuated to clamp over the proximal end of the insert, allowing the insert to be withdrawn by retracting the mandrel from within the tail section 17*b*. Once the insert is extracted, a fresh insert may be advanced into the exoskeleton using techniques described above, and the tail may be re-sealed and returned to its pocket within the body.

Figure 5F:
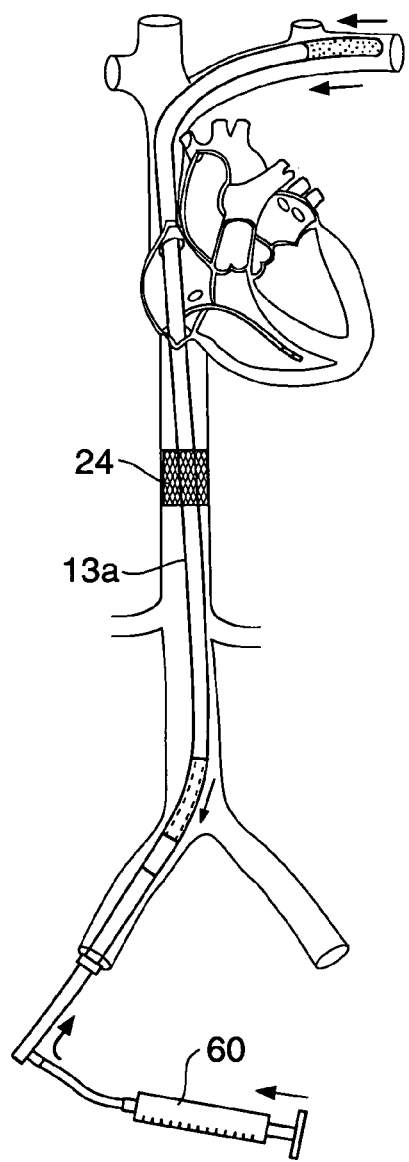
FIG. 5F is a schematic view similar to the FIG. 5A-5E views illustrating removal of the insert.

An alternative extraction method is illustrated in FIG. 5F. As shown, a syringe 60 may be coupled to the exoskeleton 13*a* and used to pump saline, carbon dioxide, or other fluid into the exoskeleton. As the injected fluid fills the distal portion of the exoskeleton, fluid pressure forces the insert towards the open end of the exoskeleton. This step may also be combined with manual extraction using a mandrel. Once the insert is extracted, a fresh component may be inserted into the exoskeleton and will displace any fluid remaining in the exoskeleton will be driven out the opening 15*a* by the advancing insert.

FIG. 6 shows an alternative embodiment of a system 110 utilizing an exoskeleton 113*a* and an insert 113*b* insertable into the exoskeleton.

In system 110, leads 114*a*, 114*b* extend from the exoskeleton 113*a* as shown. Each lead 114*a*, 114*b* is electrically connected to a contact point (not shown) that is exposed in the hollow interior of the exoskeleton 113*a*. The contact points are positioned to make electrical contact with corresponding points 122 on the surface of the interior housing when the exoskeleton 113*a* and insert 113*b* are assembled.

The exoskeleton and the insert 113*a*, 113*b* are preferably provided with means for securely engaging one another. For example, as shown in FIG. 6, threaded female and male connectors 40, 42 may be provided on the exoskeleton and inserts 113*a*, 113*b*, respectively. Following insertion of the insert 13*b* into the exoskeleton 13*a*, the insert 113*a* is rotated to engage the threads of the connectors. Additional sealing structures (e.g., o-rings) may be included on the proximal end of one or both of the components 113*a*, 113*b* to minimize flow of blood into the device. As an alternative shown in FIG. 7, threads 42*a* may be formed on the exterior surface near the distal end of the insert 113*b*, with corresponding female threads on the exoskeleton (not shown). In either case, an implantation tool (which may be similar to mandrel 28 of FIG. 2) would be connectable to the insert 113*b* and used for guiding the insert 113*b* through the vasculature and then rotating the component 113*b* to cause the corresponding threads to engage.

As yet another alternative, as shown in FIGS. 8A and 8B, insert 113*b* (FIG. 8B) may include a spring clip 44, and exoskeleton 113*a* (FIG. 8A) may include a window 46, such that when the components are assembled the clip 44 engages with the window as shown in FIG. 8C. Since clip 44 may be exposed through the window 46, it may be desirable to wire the clip 44 to function as an electrode on the exterior of the device.

As discussed, one or more o-ring seals 50 (FIGS. 7, 8A and 8C) may be used to keep fluids out of the exoskeleton. Seals (not shown) may also be used around the clip 44 to prevent fluid leakage from entering the device 112 through the window.

Figure 9:
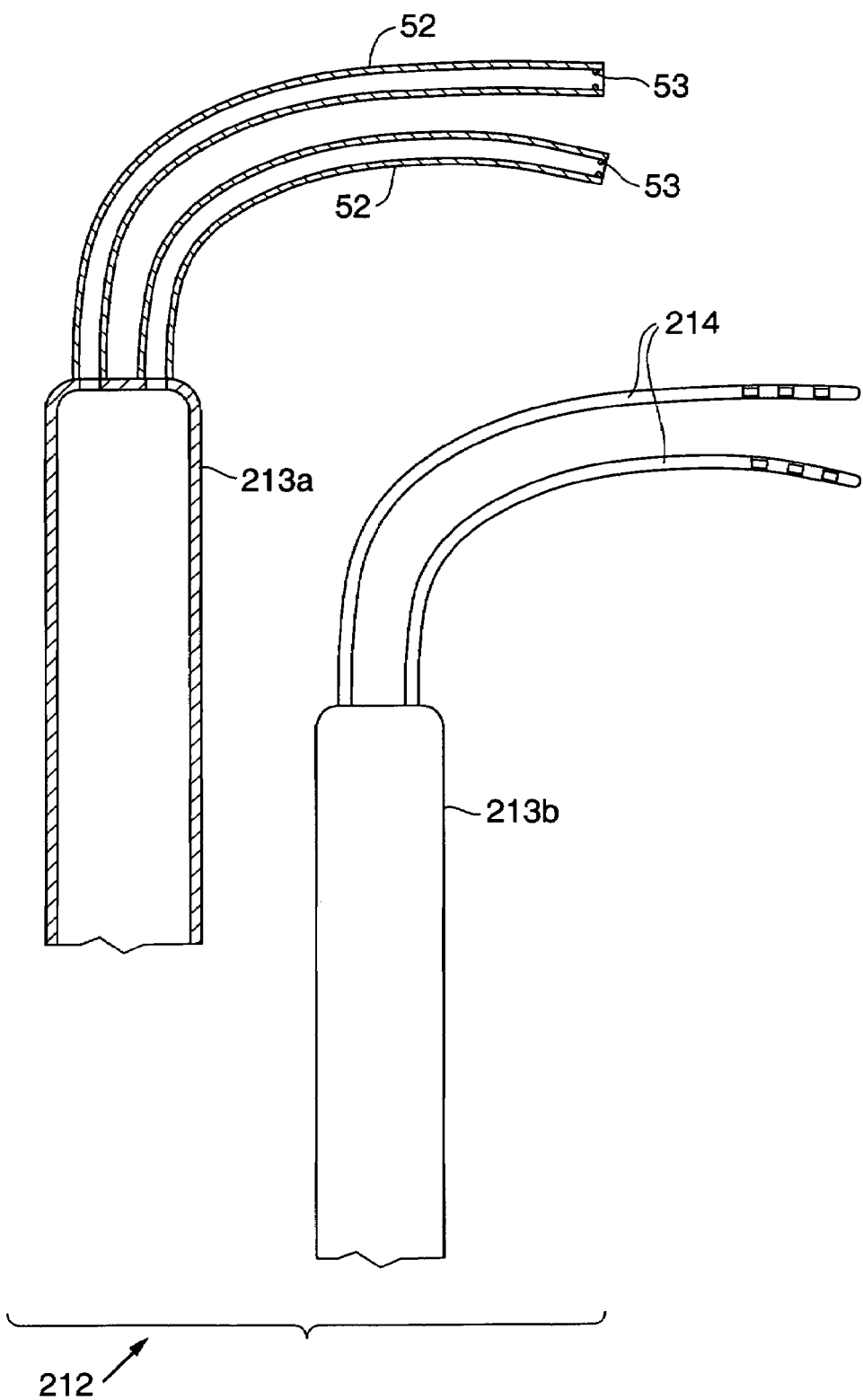
FIG. 9 is a cross-sectional side view of another embodiment of an exoskeleton and insert.

In another alternative embodiment shown in FIG. 9, leads 214 are attached to the insert 213*b*, and the exoskeleton 213*a* includes openings through which the leads may be passed during implantation. In the FIG. 9 embodiment exoskeleton 213*a* includes sleeves 52 through which the leads may be passed for this purpose. Alternatively, the exoskeleton may include holes in the distal end in place of sleeves 52.

Seals 53 (such as o-rings of the type discussed earlier) may be positioned to prevent migration of fluids into the exoskeleton via the sleeves 52.

During implantation of the system 212, leads 214 are fed through the sleeves 52 and are positioned within the heart and/or vessels in a manner similar to that described above. Fluid such as saline or gas such as carbon dioxide may be directed into the open proximal end of the exoskeleton to prevent inflow of blood or to displace blood that may have already have entered the exoskeleton during implantation. Holes or one-way valves (not shown) may also be formed in the distal region of the exoskeleton to allow any blood that may have accumulated within the exoskeleton to be displaced and evacuated as the insert is passed into the exoskeleton to facilitate retention in the body.

Drug Delivery System

The exoskeleton configuration may be adapted for use with an intravascular drug delivery system of the type described in U.S. Provisional Application No. 60/634,585, INTRAVASCULAR DELIVERY SYSTEM FOR THERAPEUTIC AGENTS, filed Dec. 9, 2004, which is incorporated herein by reference. Such a system includes an implantable drug reservoir, together with components that function to transfer drug from the reservoir into the bloodstream or into certain organs or tissues.

Components used for this purpose may include pumps, motors and batteries, and/or other components such as those listed in the '585 Provisional application.

Figure 11:
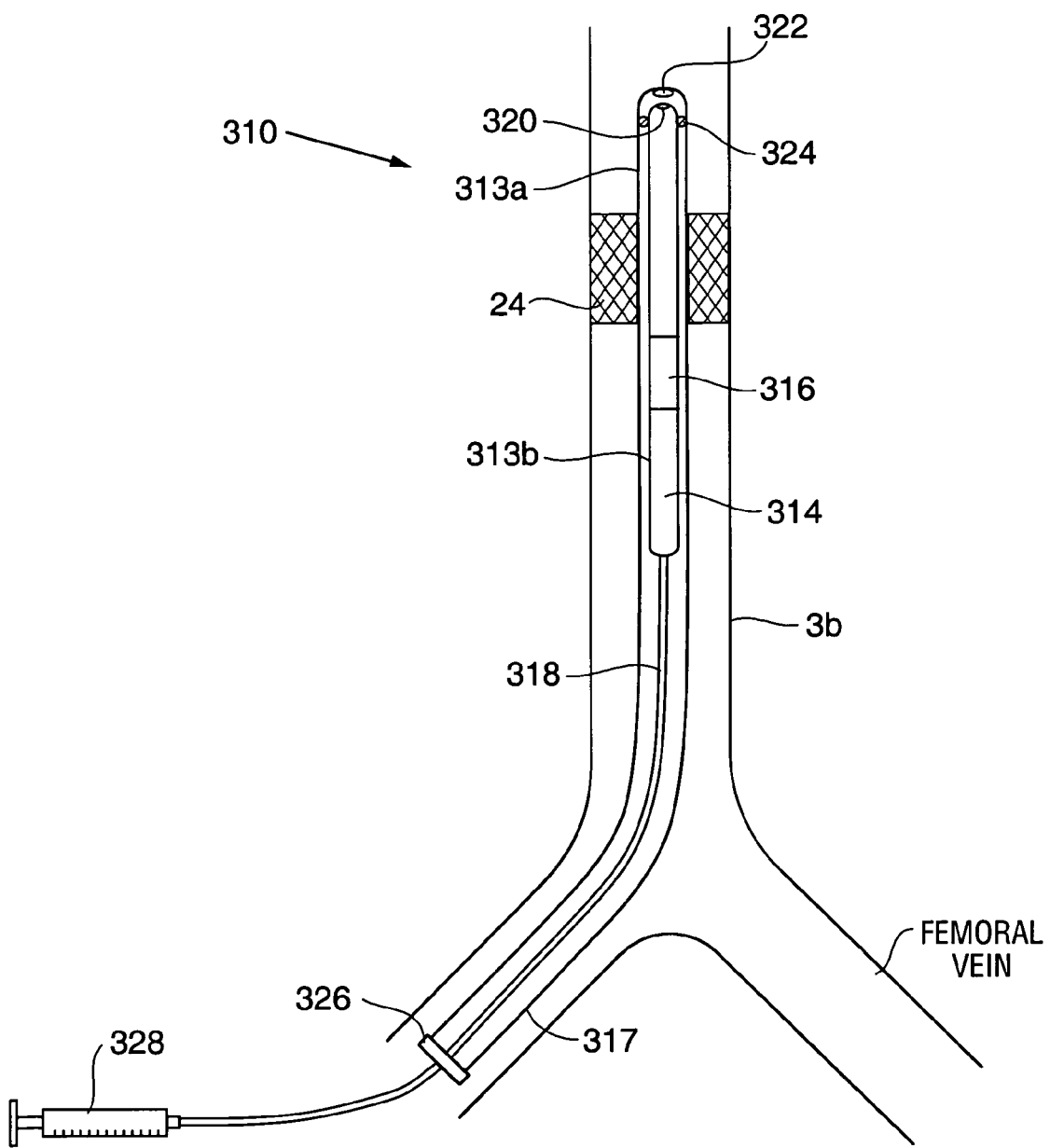
FIG. 11 illustrates an alternative embodiment of an exoskeleton and insert which form part of an intravascular drug delivery system.

Referring to FIG. 11, a system 310 may include an exoskeleton 313a and an insert 313b slidably received within the exoskeleton 313a. Insert 313b includes a drug reservoir 314 and a refill line 318 coupled to the reservoir. A pump system 316 directs agent to an exit tube or orifice 320.

Exoskeleton includes a port 322 that allows fluid released through the exit orifice 320 to pass into the bloodstream. A seal 324 may be positioned within the exoskeleton to prevent backflow of drug from exit orifice 320 into the exoskeleton 313a.

The exoskeleton may include a flexible tail portion 317 that, as described in connection with the FIG. 2 embodiment, may be tucked into the femoral vein or a subcutaneous pocket following implantation.

A subcutaneous portal 326 is fluidly coupled to the refill line 318 of reservoir, and may also function to seal the tail 317 of the exoskeleton. Portal 326 may include a one-way valve (not shown) that prevents fluid from entering the exoskeleton, or it may include a seal formed of a material that will reseal itself following puncture.

Implantation of the system 310 and replacement of the insert 313b may be performed using techniques described above. The reservoir 314 may be refilled by using a refill vessel such as a recharge syringe 328 filled with the desired drug. The needle tip of the recharge syringe may be inserted through the skin and into the subcutaneous portal 326. In this embodiment, drug reservoir within the insert 313b may be maintained at a negative pressure so as to draw the agent from the syringe once fluid communication is established. This provides feedback to the user that the syringe needle has been inserted at the proper location and can thus help to avoid injection of the agent directly into the patient in the event the portal 326 is missed by the needle.

In an alternative refill method, the tail 317 may be withdrawn from the body through a small incision, and the recharge syringe 328 or other refill device may be coupled to the portal 326 outside the body. In either case, the drug is then injected from the syringe into the reservoir via the portal 326 and refill line 318. If the system 310 is provided without a refill line and portal, the insert may instead be replaced with a new component containing a fresh supply of drug using methods described above.

In another embodiment, the insert 313b may be provided with a refill port in the insert body 313b rather than a fill line 318 extending from the insert. Such an embodiment might be refilled using a mandrel having a distal coupling including a mouth that is significantly broader than the proximal end of the device. To refill a device according to this embodiment, the mandrel would be introduced into the exoskeleton and advanced towards the insert until it passes over the proximal end of the insert. The mandrel is then clamped over the proximal end of the insert to sealingly engage the insert and to create a fluid coupling between the mandrel's fluid lumen and a refill lumen into the insert. Drug is then introduced into the mandrel for delivery into the reservoir within the insert.

Various embodiments of systems, devices and methods have been described herein. These embodiments are given only by way of example and are not intended to limit the scope of the present invention. The examples and alternatives set forth for the described components are merely examples and should not be considered to be all-inclusive lists. It should be appreciated, moreover, that the various features of the embodiments that have been described might be combined in various ways to produce numerous additional embodiments. Moreover, while various materials, dimensions, shapes, implantation locations, etc. have been described for use with disclosed embodiments, others besides those disclosed may be utilized without exceeding the scope of the invention.

What is claimed is:

1. An implantable intravascular medical system including:
   a flexible elongate sleeve proportioned and adapted for chronic implantation within a blood vessel of a patient and having an exterior surface and an interior surface defining an interior volume;
   an implantable intravascular medical device releasably positionable within the interior volume of the sleeve after implanting the sleeve in the patient, the implantable intravascular medical device including a housing and a pulse generator sealed within the housing, wherein the sleeve is separably implantable from the implantable intravascular medical device; and
   an anchor on the exterior surface of the flexible elongate sleeve, the anchor expendable into contact with an inner wall of the blood vessel.

2. The system of claim 1, wherein: the sleeve includes at least one electrode on the exterior surface and a contact positioned on the interior surface and electrically coupled to the at least one electrode; and
   wherein the housing of the implantable intravascular medical device further includes an outer surface and a conductive element on the outer surface, the conductive element being electrically coupled to the pulse generator and, positioned for electrically coupling with the contact on the interior surface of the sleeve when the implantable intravascular medical device is positioned within the interior volume of the sleeve.

3. The system of claim 1, wherein the implantable intravascular medical device is a defibrillation device.

4. The system of claim 1, wherein the implantable intravascular medical device is a pacemaker.

5. The system of claim 1, wherein the implantable intravascular medical device is a cardioverter.

6. The system of claim 1, wherein the sleeve includes an opening into the interior volume, wherein the implantable intravascular medical device is insertable into the interior volume of the sleeve through the opening, and wherein the system further includes a seal positionable in the opening to seal the interior volume against body fluids.

7. The system of claim 6, wherein the sleeve includes a side branch extending from the sleeve, wherein at least one electrode is positioned on the side branch.

8. The system of claim 6, wherein the sleeve includes a distal section and a proximal section, wherein the proximal section is more flexible than the distal section, and wherein the opening is formed in the proximal section.

9. The system of claim 1, wherein the sleeve is constructed to prevent biological growth onto the implantable intravascular medical device when the sleeve and implantable intravascular medical device are implanted in a blood vessel.

10. The system of claim 1, wherein the sleeve is formed of a material that will degrade within a blood vessel over a predetermined period of time.

11. The system of claim 1, wherein the interior surface of the sleeve includes at least one engagement feature configured to retain the implantable intravascular medical device within the sleeve.

12. An implantable intravascular medical system including:
- a flexible elongate sleeve proportioned and adapted for chronic implantation within a blood vessel of a patient and having an exterior surface, an interior surface defining an interior volume, and at least one opening into the interior volume;
- an implantable intravascular medical device insertable into the interior volume of the sleeve through the at least one opening, the implantable intravascular medical device including a housing and a pulse generator sealed within the housing;
- at least one seal positioned to seal the flexible elongate sleeve against passage of fluid into the interior volume; and
- an anchor on the exterior surface of the flexible elongate sleeve, the anchor expandable into contact with an inner wall of the blood vessel.

* * * * *